US011781907B2

(12) United States Patent
Capella et al.

(10) Patent No.: US 11,781,907 B2
(45) Date of Patent: *Oct. 10, 2023

(54) AMBIENT LIGHT DETERMINATION USING PHYSIOLOGICAL METRIC SENSOR DATA

(71) Applicant: Fitbit, Inc., San Francisco, CA (US)

(72) Inventors: Sebastian Joseph Capella, San Diego, CA (US); Shelten Gee Jao Yuen, Berkeley, CA (US); Subramaniam Venkatraman, Walnut Creek, CA (US); Félix Antoine Turgeon, Poway, CA (US); Heiko Gernot Albert Panther, Berlin (DE)

(73) Assignee: FITBIT, INC., San Francisco, CA (US)

( * ) Notice: Subject to any disclaimer, the term of this patent is extended or adjusted under 35 U.S.C. 154(b) by 77 days.

This patent is subject to a terminal disclaimer.

(21) Appl. No.: 17/340,181

(22) Filed: Jun. 7, 2021

(65) Prior Publication Data

US 2021/0293616 A1    Sep. 23, 2021

Related U.S. Application Data

(63) Continuation of application No. 15/828,209, filed on Nov. 30, 2017, now Pat. No. 11,029,199, which is a (Continued)

(51) Int. Cl.
*G01J 1/42* (2006.01)
*A61B 5/1455* (2006.01)
(Continued)

(52) U.S. Cl.
CPC .......... *G01J 1/4204* (2013.01); *A61B 5/1455* (2013.01); *A61B 5/681* (2013.01); *A61B 5/742* (2013.01);
(Continued)

(58) Field of Classification Search
CPC ......... A61B 5/1455; A61B 5/74; A61B 5/742; G01J 1/4204
See application file for complete search history.

(56) References Cited

U.S. PATENT DOCUMENTS

| 4,367,752 A | 1/1983 | Jimenez et al. |
| 4,771,792 A | 9/1988 | Seale |

(Continued)

FOREIGN PATENT DOCUMENTS

| EP | 1 721 237 B1 | 8/2012 |
| KR | 10-1599288 B1 | 10/2015 |

(Continued)

OTHER PUBLICATIONS

U.S. Appl. No. 14/073,657, filed Nov. 6, 2013.
(Continued)

*Primary Examiner* — Eric F Winakur
(74) *Attorney, Agent, or Firm* — Dority & Manning, P.A.

(57) ABSTRACT

A wearable computing device includes an electronic display with a configurable brightness level setting, a physiological metric sensor system including a light source configured to direct light into tissue of a user wearing the wearable computing device and a light detector configured to detect light from the light source that reflects back from the user. The device may further include control circuitry configured to activate the light source during a first period, generate a first light detector signal indicating a first amount of light detected by the light detector during the first period, deactivate the light source during a second period, generate a second light detector signal indicating a second amount of light detected by the light detector during the second period, generate a physiological metric based at least in part on the first light detector signal and the second light detector signal, (Continued)

and modify the configurable brightness level setting based on the second light detector signal.

19 Claims, 20 Drawing Sheets

Related U.S. Application Data continuation-in-part of application No. 15/436,440, filed on Feb. 17, 2017, now Pat. No. 10,209,365, which is a continuation of application No. 14/940,072, filed on Nov. 12, 2015, now Pat. No. 9,572,533, which is a continuation of application No. 14/700,069, filed on Apr. 29, 2015, now Pat. No. 9,198,604, which is a continuation of application No. 14/290,909, filed on May 29, 2014, now Pat. No. 9,044,171, said application No. 15/828,209 is a continuation-in-part of application No. 15/436,440, filed on Feb. 17, 2017, now Pat. No. 10,209,365, which is a continuation-in-part of application No. 13/924,784, filed on Jun. 24, 2013, now Pat. No. 8,954,135.

(60) Provisional application No. 62/428,158, filed on Nov. 30, 2016, provisional application No. 61/973,614, filed on Apr. 1, 2014, provisional application No. 61/955,045, filed on Mar. 18, 2014, provisional application No. 61/946,439, filed on Feb. 28, 2014, provisional application No. 61/830,600, filed on Jun. 3, 2013, provisional application No. 61/752,826, filed on Jan. 15, 2013, provisional application No. 61/662,961, filed on Jun. 22, 2012.

(51) Int. Cl.
| | |
|---|---|
| *G09G 5/10* | (2006.01) |
| *A61B 5/00* | (2006.01) |
| *G01J 1/32* | (2006.01) |
| *G01J 1/18* | (2006.01) |
| *G01J 1/44* | (2006.01) |
| *G01J 1/46* | (2006.01) |
| *G01J 1/02* | (2006.01) |
| *G01J 1/04* | (2006.01) |
| *G06V 10/141* | (2022.01) |
| *A61B 5/024* | (2006.01) |
| *A61B 5/021* | (2006.01) |
| *A61B 5/145* | (2006.01) |
| *A61B 5/0533* | (2021.01) |
| *A61B 5/01* | (2006.01) |
| *G06V 40/10* | (2022.01) |

(52) U.S. Cl.
CPC ......... *G01J 1/0204* (2013.01); *G01J 1/0219* (2013.01); *G01J 1/0271* (2013.01); *G01J 1/0407* (2013.01); *G01J 1/18* (2013.01); *G01J 1/32* (2013.01); *G01J 1/44* (2013.01); *G01J 1/46* (2013.01); *G06V 10/141* (2022.01); *G09G 5/10* (2013.01); *A61B 5/01* (2013.01); *A61B 5/021* (2013.01); *A61B 5/024* (2013.01); *A61B 5/02405* (2013.01); *A61B 5/0533* (2013.01); *A61B 5/14532* (2013.01); *A61B 5/489* (2013.01); *G01J 2001/0257* (2013.01); *G01J 2001/182* (2013.01); *G01J 2001/444* (2013.01); *G01J 2001/4406* (2013.01); *G06V 40/15* (2022.01); *G09G 2320/0626* (2013.01); *G09G 2354/00* (2013.01); *G09G 2360/144* (2013.01); *G09G 2380/08* (2013.01)

(56) References Cited

U.S. PATENT DOCUMENTS

| | | |
|---|---|---|
| 5,036,856 A | 8/1991 | Thornton |
| 5,101,831 A | 4/1992 | Koyama et al. |
| 5,318,597 A | 6/1994 | Hauck et al. |
| 5,738,104 A | 4/1998 | Lo et al. |
| 5,828,336 A | 10/1998 | Yunck et al. |
| 5,963,167 A | 10/1999 | Lichten et al. |
| 6,131,076 A | 10/2000 | Stephan et al. |
| 6,241,684 B1 | 6/2001 | Amano et al. |
| 6,418,394 B1 | 7/2002 | Puolakanaho et al. |
| 6,583,369 B2 | 6/2003 | Montagnino et al. |
| 6,720,860 B1 | 4/2004 | Narayanaswami |
| 6,731,967 B1 | 5/2004 | Turcott |
| 7,539,532 B2 | 5/2009 | Tran |
| 7,558,678 B2 | 7/2009 | Jones |
| 7,570,962 B2 | 8/2009 | Chou |
| 7,616,153 B2 | 11/2009 | Honda et al. |
| 7,706,977 B2 | 4/2010 | Soehren |
| 8,152,745 B2 | 4/2012 | Smith et al. |
| 8,211,503 B2 | 7/2012 | Tsao et al. |
| 8,346,328 B2 | 1/2013 | Mannheimer et al. |
| 8,386,042 B2 | 2/2013 | Yudovsky et al. |
| 8,417,300 B2 | 4/2013 | Wong et al. |
| 8,444,578 B2 | 5/2013 | Bourget et al. |
| 8,475,367 B1 | 7/2013 | Yuen et al. |
| 8,579,827 B1 | 11/2013 | Rulkov et al. |
| 8,630,798 B2 | 1/2014 | Hani et al. |
| 8,684,900 B2 | 4/2014 | Tran |
| 8,762,059 B1 | 6/2014 | Balogh |
| 8,764,651 B2 | 7/2014 | Tran |
| 8,792,981 B2 | 7/2014 | Yudovsky et al. |
| 8,920,332 B2 | 12/2014 | Hong et al. |
| 8,945,017 B2 | 2/2015 | Venkatraman et al. |
| 8,948,832 B2 | 2/2015 | Hong et al. |
| 8,956,303 B2 | 2/2015 | Hong et al. |
| 8,976,062 B2 | 3/2015 | Park et al. |
| 8,998,815 B2 | 4/2015 | Venkatraman et al. |
| 9,005,129 B2 | 4/2015 | Venkatraman et al. |
| 9,013,351 B2 | 4/2015 | Park et al. |
| 9,035,825 B2 | 5/2015 | Park et al. |
| 9,044,149 B2 | 6/2015 | Richards et al. |
| 9,044,150 B2 | 6/2015 | Brumback et al. |
| 9,044,171 B2 | 6/2015 | Venkatraman et al. |
| 9,113,794 B2 | 8/2015 | Hong et al. |
| 9,113,795 B2 | 8/2015 | Hong et al. |
| 9,198,604 B2 | 12/2015 | Venkatraman et al. |
| 9,237,855 B2 | 1/2016 | Hong et al. |
| 9,297,903 B2 | 3/2016 | Park et al. |
| 9,572,533 B2 | 2/2017 | Venkatraman |
| 2001/0044588 A1 | 11/2001 | Mault |
| 2002/0168985 A1 | 11/2002 | Zhao et al. |
| 2003/0018430 A1 | 1/2003 | Ladetto et al. |
| 2004/0236227 A1 | 11/2004 | Gueissaz |
| 2005/0054940 A1 | 3/2005 | Almen |
| 2005/0245793 A1 | 11/2005 | Hilton et al. |
| 2006/0028429 A1 | 2/2006 | Kanevsky |
| 2006/0287824 A1 | 12/2006 | Lin |
| 2008/0097221 A1 | 4/2008 | Florian |
| 2008/0249836 A1 | 10/2008 | Angell et al. |
| 2008/0287751 A1 | 11/2008 | Stivoric et al. |
| 2009/0012433 A1 | 1/2009 | Fernstrom et al. |
| 2009/0048044 A1 | 2/2009 | Oleson et al. |
| 2009/0303118 A1 | 12/2009 | Corazza et al. |
| 2009/0315773 A1 | 12/2009 | Tomita |
| 2010/0062792 A1 | 3/2010 | Han |
| 2010/0106044 A1 | 4/2010 | Linderman |
| 2010/0152600 A1 | 6/2010 | Droitcour et al. |
| 2010/0187406 A1 | 7/2010 | Van Dalen et al. |
| 2010/0249633 A1 | 9/2010 | Droitcour et al. |
| 2010/0273419 A1 | 10/2010 | Rajagopal et al. |
| 2010/0292568 A1 | 11/2010 | Droitcour et al. |
| 2010/0298650 A1 | 11/2010 | Moon et al. |
| 2010/0298651 A1 | 11/2010 | Moon et al. |
| 2010/0298653 A1 | 11/2010 | McCombie et al. |
| 2010/0331145 A1 | 12/2010 | Lakovic et al. |
| 2010/0331657 A1 | 12/2010 | Mensinger et al. |

(56) References Cited

U.S. PATENT DOCUMENTS

| | | |
|---|---|---|
| 2011/0009727 A1 | 1/2011 | Mensinger et al. |
| 2011/0032105 A1 | 2/2011 | Hoffman et al. |
| 2011/0066010 A1 | 3/2011 | Moon et al. |
| 2011/0090081 A1 | 4/2011 | Khorashadi et al. |
| 2011/0163914 A1 | 7/2011 | Seymour |
| 2011/0267230 A1 | 11/2011 | LaMance et al. |
| 2011/0282168 A1 | 11/2011 | Weiss et al. |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0123232 A1 | 5/2012 | Najarian et al. |
| 2012/0150074 A1 | 6/2012 | Yanev et al. |
| 2012/0172733 A1 | 7/2012 | Park |
| 2012/0226471 A1 | 9/2012 | Yuen et al. |
| 2012/0226472 A1 | 9/2012 | Yuen et al. |
| 2012/0232432 A1 | 9/2012 | Kahn et al. |
| 2012/0245439 A1 | 9/2012 | Andre et al. |
| 2012/0253663 A1 | 10/2012 | Hani et al. |
| 2012/0255875 A1 | 10/2012 | Vincente et al. |
| 2012/0274508 A1 | 11/2012 | Brown et al. |
| 2012/0303390 A1 | 11/2012 | Brook et al. |
| 2012/0316471 A1 | 12/2012 | Rahman et al. |
| 2013/0009779 A1 | 1/2013 | Wittling et al. |
| 2013/0073254 A1 | 3/2013 | Yuen et al. |
| 2013/0073255 A1 | 3/2013 | Yuen et al. |
| 2013/0077826 A1 | 3/2013 | Cowperthwaite et al. |
| 2013/0080113 A1 | 3/2013 | Yuen et al. |
| 2013/0106684 A1 | 5/2013 | Weast et al. |
| 2013/0138458 A1 | 5/2013 | Lorsch |
| 2013/0151196 A1 | 6/2013 | Yuen et al. |
| 2013/0158369 A1 | 6/2013 | Yuen et al. |
| 2013/0159223 A1 | 6/2013 | Bahl et al. |
| 2013/0163390 A1 | 6/2013 | Gossweiler, III et al. |
| 2013/0215229 A1 | 8/2013 | Yerli |
| 2013/0280682 A1 | 10/2013 | Levine et al. |
| 2014/0073486 A1 | 3/2014 | Ahmed et al. |
| 2014/0099614 A1 | 4/2014 | Hu et al. |
| 2014/0125491 A1 | 5/2014 | Park et al. |
| 2014/0127996 A1 | 5/2014 | Park et al. |
| 2014/0135631 A1 | 5/2014 | Brumback et al. |
| 2014/0142403 A1 | 5/2014 | Brumback et al. |
| 2014/0160033 A1 | 6/2014 | Brikman et al. |
| 2014/0179298 A1 | 6/2014 | Grokop et al. |
| 2014/0180022 A1 | 6/2014 | Stirovic et al. |
| 2014/0180621 A1 | 6/2014 | Poduri et al. |
| 2014/0206327 A1 | 7/2014 | Ziemianska et al. |
| 2014/0275821 A1 | 9/2014 | Beckman |
| 2014/0275850 A1 | 9/2014 | Venkatraman et al. |
| 2014/0275852 A1 | 9/2014 | Hong et al. |
| 2014/0275854 A1 | 9/2014 | Venkatraman et al. |
| 2014/0276119 A1 | 9/2014 | Venkatraman et al. |
| 2014/0278139 A1 | 9/2014 | Hong et al. |
| 2014/0288390 A1 | 9/2014 | Hong et al. |
| 2014/0288391 A1 | 9/2014 | Hong et al. |
| 2014/0288392 A1 | 9/2014 | Hong et al. |
| 2014/0288435 A1 | 9/2014 | Richards et al. |
| 2014/0288436 A1 | 9/2014 | Venkatraman et al. |
| 2014/0288438 A1 | 9/2014 | Venkatraman et al. |
| 2014/0292564 A1 | 10/2014 | Park et al. |
| 2014/0292565 A1 | 10/2014 | Park et al. |
| 2014/0292566 A1 | 10/2014 | Park et al. |
| 2014/0293059 A1 | 10/2014 | Park et al. |
| 2014/0303523 A1 | 10/2014 | Hong et al. |
| 2014/0316305 A1 | 10/2014 | Venkatraman et al. |
| 2014/0378786 A1 | 12/2014 | Hong et al. |
| 2014/0378872 A1 | 12/2014 | Hong et al. |
| 2015/0026647 A1 | 1/2015 | Park et al. |
| 2015/0146355 A1 | 5/2015 | Goyal et al. |
| 2015/0230735 A1 | 8/2015 | Venkatraman et al. |
| 2015/0342529 A1 | 12/2015 | Gassoway |
| 2017/0188893 A1 | 7/2017 | Venkatraman et al. |

FOREIGN PATENT DOCUMENTS

| | | |
|---|---|---|
| WO | WO 2012/170586 A2 | 12/2012 |
| WO | WO 2012/170587 A2 | 12/2012 |
| WO | WO 2012/170924 A2 | 12/2012 |
| WO | WO 2012/171032 A2 | 12/2012 |
| WO | WO 2015/073747 A1 | 5/2015 |
| WO | WO 2015/127067 A1 | 8/2015 |
| WO | WO 2016/003269 A1 | 1/2016 |

OTHER PUBLICATIONS

U.S. Appl. No. 14/073,702, filed Nov. 6, 2013.
U.S. Appl. No. 14/154,009, filed Jan. 13, 2014.
U.S. Appl. No. 14/154,019, filed Jan. 13, 2014.
U.S. Appl. No. 14/214,655, filed Mar. 14, 2014.
U.S. Appl. No. 14/216,743, filed Mar. 17, 2014.
U.S. Appl. No. 14/242,711, filed Apr. 1, 2014.
U.S. Appl. No. 14/250,256, filed Apr. 10, 2014.
U.S. Appl. No. 14/265,202, filed Apr. 29, 2014.
U.S. Appl. No. 14/265,205, filed Apr. 29, 2014.
U.S. Appl. No. 14/265,208, filed Apr. 29, 2014.
U.S. Appl. No. 14/290,884, filed May 29, 2014.
U.S. Appl. No. 14/290,915, filed May 29, 2014.
U.S. Appl. No. 14/292,669, filed May 30, 2014.
U.S. Appl. No. 14/292,673, filed May 30, 2014.
U.S. Appl. No. 14/295,059, filed Jun. 3, 2014.
U.S. Appl. No. 14/295,076, filed Jun. 3, 2014.
U.S. Appl. No. 14/295,122, filed Jun. 3, 2014.
U.S. Appl. No. 14/295,144, filed Jun. 3, 2014.
U.S. Appl. No. 14/295,158, filed Jun. 3, 2014.
U.S. Appl. No. 14/295,161, filed Jun. 3, 2014.
U.S. Appl. No. 14/481,020, filed Sep. 9, 2014.
U.S. Appl. No. 14/481,762, filed Sep. 9, 2014.
U.S. Appl. No. 14/484,104, filed Sep. 11, 2014.
U.S. Appl. No. 14/507,173, filed Oct. 6, 2014.
U.S. Appl. No. 14/507,184, filed Oct. 6, 2014.
Cooper, Aug. 16, 2013, Withings Pulse review, http://www.engadget.com/2013/08/16/withings-pulse-revew/, 8 pages.
Dcrainmaker, "Gaimin Swim watch In-Depth Review," Jun. 25, 2012 updated Feb. 16, 2013, http://www.dcrainmaker.com/2012/06/garmin-swim-in-depth-review.html, 38 pages.
dcrainmaker.com, "Basis B1 Watch In-Depth Review", Jul. 25, 2013, http://www.dcrainmaker.com/2013/07 /basis-b1-review.html, retrieved Feb. 4, 2014, 56 pages.
dcrainmaker.com, "Gaimin Swim watch In-Depth Review," Jun. 25, 2012, updated Feb. 16, 2013, http://fwww.dcrainmaker.com/2012/06/garmin-swim-in-depth-review.html, retrieved on Sep. 9, 2013, 38 pages.
Fitbit User's Manual, Last Updated Oct. 22, 2009, 15 pages.
Forerunner® 10 Owner's Manual, Aug. 2012, Garmin Ltd., 10 pages.
Forerunner® 110 Owner's Manual, (2010) "GPS-Enabled Sport Watch," Garmin Ltd., 16 pages.
Forerunner® 201 personal trainer owner's manual, Feb. 2006, Garmin Ltd., 48 pages.
Forerunner® 205/305 Owner's Manual, GPS-enabled trainer for runners, 2006-2008, Garmin Ltd., 80 pages.
Forerunner® 210 Owner's Manual, 2010, "GPS-Enabled Sport Watch," Garmin Ltd., 28 pages.
Forerunner® 301 personal trainer owner's manual, Feb. 2006, Garmin Ltd., 66 pages.
Forerunner® 310XT Owner's Manual, Mul Tisport GPS Training Device, 2009-2013, Garmin Ltd., 56 pages.
Forerunner® 405 Owner's Manual, Mar. 2011, "GPS-Enabled Sport Watch With Wireless Sync," Garmin Ltd., 56 pages.
Forerunner® 405CX Owner's Manual, "GPS-Enabled Sports Watch With Wireless Sync," Mar. 2009, Garmin Ltd., 56 pages.
Forerunner® 410 Owner's Manual, Jul. 2012, "GPS-Enabled Sport Watch With Wireless Sync," Garmin Ltd., 52 pages.
Forerunner® 50 with ANT +Sport™ wireless technology, Owner's Manual, Nov. 2007, Garmin Ltd., 44 pages.

(56) References Cited

OTHER PUBLICATIONS

Forerunner® 910XT Owner's Manual, Jan. 2013, Garmin Ltd., 56 pages.
Garmin Swim™ Owner's Manual Jun. 2012, 12 pages.
Iphone-tip-and-advice.com, "Activator is One of the Best Cydia iPhone Hacks I Control your iPhone with Gestures," http://www.iphone-tips-and-advice.com/activatior.html, retrieved on Jul. 9, 2013, 10 pp.
Jawbone UP, "Parts of Your Band," 2013 Jawbone UP Band, downloaded Jul. 22, 2013, 1 page.
Lark/Larkpro, User Manual, 2012 "What's in the box," Lark Technologies, 7 pages.
Larklife, User Manual, 2012 Lark Technologies, 7 pages.
Lifetrnr, User Manual, 2003, specific date unknown, NB new balance®, Implus Footcare, LLC, 3 pages.
Nike+ FuelBand GPS Manual, User's Guide, Product Release Date Unknown, downloaded Jul. 22, 2013, 26 pages.
Nike+SportBand User's Guide, Product Release Date Unknown, downloaded Jul. 22, 2013, 36 pages.
Nike+SportWatoh GPS Manual, User's Guide, Powered by TOMTOM, Product Release Date Unknown, downloaded Jul. 22, 2013, 42 pages.
Notice of Allowance (Corrected Notice of Allowability), U.S. Appl. No. 14/292,669, dated Oct. 14, 2014.
Notice of Allowance, U.S. Appl. No. 14/290,909, dated Jan. 29, 2015, 6 pages.
Notice of Allowance, U.S. Appl. No. 14/292,669, dated Sep. 23, 2014.
Notice of Allowance, U.S. Appl. No. 14/292,673, dated Dec. 8, 2014.
Notice of Allowance, U.S. Appl. No. 14/295,122, dated Nov. 24, 2014.
Notice of Allowance, U.S. Appl. No. 14/295,144, dated Dec. 3, 2014.
Notice of Allowance, U.S. Appl. No. 14/295,144, dated Oct. 14, 2014.
Notice of Allowance, U.S. Appl. No. 14/295,158, dated Sep. 26, 2014.
Notice of Allowance, U.S. Appl. No. 14/700,069, dated Jul. 23, 2015, 26 pages.
Office Action, U.S. Appl. No. 14/073,657, dated Mar. 13, 2014.
Office Action, U.S. Appl. No. 14/154,009, dated Mar. 14, 2014.
Office Action, U.S. Appl. No. 14/154,009, dated Sep. 29, 2014.
Office Action, U.S. Appl. No. 14/154,019, dated Nov. 25, 2014.
Office Action, U.S. Appl. No. 14/216,743, dated Dec. 4, 2014.
Office Action, U.S. Appl. No. 14/242,711, dated Jul. 9, 2014.
Office Action, U.S. Appl. No. 14/250,256, dated Aug. 22, 2014.
Office Action, U.S. Appl. No. 14/256,202, dated Aug. 15, 2014.
Office Action, U.S. Appl. No. 14/265,205, dated Jul. 17, 2014.
Office Action, U.S. Appl. No. 14/265,208, dated Aug. 15, 2014.
Office Action, U.S. Appl. No. 14/290,884, dated Oct. 22, 2014.
Office Action, U.S. Appl. No. 14/290,909, dated Oct. 22, 2014, 12 pages.
Office Action, U.S. Appl. No. 14/290,912, dated Feb. 25, 2015, 28 pages.
Office Action, U.S. Appl. No. 14/290,912, dated Jul. 28, 2015, 26 pages.
Office Action, U.S. Appl. No. 14/290,912, filed Jul. 28, 2015, 26 pages.
Office Action, U.S. Appl. No. 14/292,673, filed Aug. 5, 2014.
Office Action, Application No. 14/295,059, dated Sep. 18, 2014.
Office Action, Application No. 14/295,122, dated Jul. 31, 2014.
Office Action, U.S. Appl. No. 14/481,762, dated Oct. 7, 2014.
Office Action, U.S. Appl. No. 14/484,104, dated Dec. 10, 2014.
Patel et al., "A Review of Wearable Sensors and Systems with Application in Rehabilitation", 2012, Journal of Neuro Engineering and Rehabilitation, 17 pages.
Polar WearLink® + Coded Transmitter 31 Coded Transmitter W.I.N.D. User Manual, Polar® Listen to Your Body, Manufactured by Polar Electro Oy, 11 pages.
techcrunch.com, "Basis Reveals An Awesome New Affordable Heart, and Health Tracker You Can Wear On Your Wrist," Empson, Sep. 22, 2011, http://techcrunch.com/2011/09/22/basis-reveals-an-awesomenew, retrieved on Sep. 23, 2013, 3 pages.
techlicious.com, "Which New Activity Tracker is Best for You?", Desmarais, http://www.techlicious.com/guide/whichnew-activity-tracker-is-right-for-you/, posted on Sep. 3, 2013, Health and Home, Health & Fitness, Guides & Reviews, retrieved on Sep. 23, 2013, 4 pages.
thewiredself.com, "Basis Wristband Make Its Debut", Chudnow, Dec. 3, 2012, http://thewiredself.com/health/basis-wrist-band-make-its-debut/retrieved on Jul. 22, 2013, 3 pages.
U.S. Final Office Action, U.S. Appl. No. 14/250,256, dated Nov. 21, 2014.
Wikipedia, "Assisted GPS,", http://en.wikipedia.org/wiki/Assisted GPS, retrieved on Apr. 2, 2014, 4 pages.
Wikipedia, "Global Positioning System," https://en.wikipedia.org/wiki/Global_Positioning_System, retrieved on Apr. 2, 2014, 23 pages.
Wikipedia, "GPS navigation device," http://en.wikipedia.org/wiki/GPS navigation device, retrieved on Apr. 2, 2014, 8 pages.
Wikipedia, "GPS signals." http://en.wikipedia.org/wiki/GPS signals, retrieved on Apr. 2, 2014, 12 pages.
withings.com/pulse, "Withings pulse, Quick Installation Guide", Jul. 24, 2013, Withings Pulse QIG, v 1.3, 16 pages.
Zhou et al., "IODetector: A Generic Sendee for Indoor Outdoor Detection" Nov. 6-9, 2012, SenSys' 12, Toronto, ON, Canada, 14 pages.
Zijlstra et al., "Assessment of spatio-temporal parameters during unconstrained walking," Eur J Appl Physiol, 2004, vol. 92, pp. 39-44.

AMBIENT LIGHT DETERMINATION USING PHYSIOLOGICAL METRIC SENSOR DATA

PRIORITY CLAIM

This application is a continuation of U.S. application Ser. No. 15/828,209 filed on Nov. 30, 2017, entitled AMBIENT LIGHT DETERMINATION USING PHYSIOLOGICAL METRIC SENSOR DATA, which is a continuation-in-part of U.S. application Ser. No. 15/436,440 filed Feb. 17, 2017, issued as U.S. Pat. No. 10,209,365, entitled GPS POWER CONSERVATION USING ENVIRONMENTAL DATA, which is a continuation of U.S. application Ser. No. 14/940,072 entitled GPS POWER CONSERVATION USING ENVIRONMENTAL DATA, filed on Nov. 12, 2015, issued as U.S. Pat. No. 9,572,533, which is a continuation of U.S. application Ser. No. 14/700,069 entitled GPS POWER CONSERVATION USING ENVIRONMENTAL DATA, filed on Apr. 29, 2015, issued as U.S. Pat. No. 9,198,604, which is a continuation of U.S. application Ser. No. 14/290,909 entitled GPS POWER CONSERVATION USING ENVIRONMENTAL DATA filed on May 29, 2014, issued as U.S. Pat. No. 9,044,171, U.S. application Ser. No. 14/290,909 claims the benefit of priority under 35 U.S.C. § 119(e) to U.S. Provisional Patent Application Nos. 61/973,614 entitled GPS ACCURACY REFINEMENT USING EXTERNAL SENSORS filed Apr. 1, 2014, 61/955,045 entitled GPS POWER CONSERVATION USING ENVIRONMENTAL DATA filed on Mar. 18, 2014, 61/946,439 entitled HEART RATE DATA COLLECTION filed on Feb. 28, 2014, and 61/830,600 entitled PORTABLE MONITORING DEVICES AND METHODS OF OPERATING SAME, filed on Jun. 3, 2013. U.S. application Ser. No. 15/828,209 filed on Nov. 30, 2017, entitled AMBIENT LIGHT DETERMINATION USING PHYSIOLOGICAL METRIC SENSOR DATA, is a continuation-in-part of U.S. application Ser. No. 15/436,440, U.S. application Ser. No. 13/924,784 entitled PORTABLE BIOMETRIC MONITORING DEVICES AND METHODS OF OPERATING SAME filed on Jun. 24, 2013, issued as U.S. Pat. No. 8,954,135; U.S. application Ser. No. 13/924,784 claims the benefit of priority under 35 U.S.C. § 119(e) to U.S. Provisional Application Ser. No. 61/752,826 entitled PORTABLE BIOMETRIC MONITORING DEVICES AND METHODS OF OPERATING SAME filed on Jan. 15, 2013 and 61/662,961 entitled WIRELESS PERSONAL BIOMETRICS MONITOR filed on Jun. 22, 2012. U.S. application Ser. No. 15/828,209 also claims the benefit of priority under 35 U.S.C. § 119(e) to U.S. Provisional Application Ser. No. 62/428,158 filed Nov. 30, 2016 entitled AMBIENT LIGHT DETERMINATION USING PHYSIOLOGICAL METRIC SENSOR DATA. The entirety of the above herein incorporated by reference.

BACKGROUND

Field

The present disclosure generally relates to the field of wearable electronic devices.

Description of Related Art

Wearable electronic devices can generate and/or provide information related to physiological metrics associated with a user. Information may be presented to the user through the use of an electronic display that is illuminated using a display illumination component.

SUMMARY

In some implementations, the present disclosure relates to a wearable computing device comprising an electronic display with a configurable brightness level setting, a physiological metric sensor system including a light source configured to direct light into tissue of a user when the user is wearing the wearable computing device and a light detector configured to detect light from the light source that reflects back from the user, and control circuitry. The control circuitry is configured to activate the light source during a first period, generate a first light detector signal indicating a first amount of light detected by the light detector during the first period, deactivate the light source during a second period, generate a second light detector signal indicating a second amount of light detected by the light detector during the second period, generate a physiological metric based at least in part on the first light detector signal and the second light detector signal, and modify the configurable brightness level setting based at least in part on the second light detector signal.

The control circuitry may be further configured to determine one or more physiological characteristics of the user, adjust one or more illumination parameters of the light source based on the determined one or more physiological characteristics and adjust one or more reception parameters of the light detector based on the determined one or more physiological characteristics.

In some embodiments, the control circuitry is further configured to adjust the one or more reception parameters of the light detector before generating the second light detector signal. The control circuitry may be further configured to adjust the one or more illumination parameters and to adjust the one or more reception parameters before activating the light source during the first period.

The control circuitry may be configured to generate the physiological metric at least in part by partially cancelling an effect of ambient light on the first light detector signal. For example, cancelling the effect of ambient light on the first light detector signal may involve subtracting out the second amount of light from the first amount of light. In certain embodiments, the control circuitry is configured to generate the first light detector signal and the second light detector signal using a transimpedance amplifier coupled to sample-and-hold circuitry. The electronic display may be associated with a first (e.g., front) side of the wearable computing device and the light source and light detector may be associated with a second (e.g., back) side of the wearable computing device.

Modifying the configurable brightness level setting may involve changing the configurable brightness level setting from a first mode to a second mode. In certain embodiments, the first mode corresponds to an outdoor lighting condition and the second mode corresponds to an indoor lighting condition. In certain embodiments, the first mode corresponds to an indoor lighting condition and the second mode corresponds to an outdoor lighting condition. The second mode may be associated with a relatively higher brightness compared to the first mode. Alternatively, the second mode may be associated with a relatively lower brightness compared to the first mode. The control circuitry may be further configured to lock the configurable brightness level setting of the electronic display in the second mode until the electronic display is powered down. In certain embodiments, the first mode and the second mode are a subset of a group of three or more operational brightness modes for the electronic display.

In certain embodiments, the light source comprises a plurality of LED light sources. In certain embodiments, the control circuitry is further configured to determine whether an amplitude of the second light detector signal is greater than a threshold value, wherein said modifying the configurable brightness level setting is based at least in part on said determination.

In some implementations, the present disclosure relates to a biometric monitoring device comprising an electronic display associated with a first (e.g., front) side of the biometric monitoring device, the electronic display having a configurable brightness level setting, and a physiological metric sensor system including a light source and a light detector associated with a second (e.g., back) side of the biometric monitoring device. The physiological metric sensor system is configured to generate a physiological metric signal at least in part by directing light from the light source into a user during a first period of time, detecting a first amount of light during the first period of time, the first amount of light including reflected light from the light source and first ambient light, detecting a second amount of light during a second period of time using the light detector, the second amount of light including second ambient light, and at least partially cancelling the first ambient light in the first amount of light based on the second amount of light. The biometric monitoring device further comprises control circuitry configured to adjust the configurable brightness level setting of the electronic display based at least in part on the second amount of light.

The physiological metric sensor system may be configured to generate the physiological metric signal substantially continuously. In certain embodiments, the second period of time occurs temporally before the first period of time.

In some embodiments, the control circuitry of the biometric monitoring device is further configured to determine one or more physiological characteristics of the user, adjust one or more illumination parameters of the light source based on the determined one or more physiological characteristics and adjust one or more reception parameters of the light detector based on the determined one or more physiological characteristics.

In some implementations, the present disclosure relates to a method of managing power in a wearable computing device. The method comprises directing light from a light source into tissue of a user during a first time period, generating a first light detector signal using a skin-facing light detector, the first light detector signal indicating a first amount of light detected by the light detector during the first period, deactivating the light source during a second period, generating a second light detector signal using the skin-facing light detector, the second light detector signal indicating a second amount of light detected by the light detector during the second period, generating a physiological metric signal based at least in part on the first light detector signal and the second light detector signal, and modifying a brightness level of an electronic display based at least in part on the second light detector signal.

Generating the physiological metric signal may comprise generating an ambient light cancellation signal based on the second light detector signal and cancelling ambient light in the first light detector signal using the ambient light cancellation signal. In certain embodiments, generating the ambient light cancellation signal further comprises conditioning the second light detector signal to account for skin tone characteristics of the user. The method may further comprise at least partially reversing the conditioning of the second light detector signal to produce a raw ambient light signal, wherein said modifying the brightness level of the electronic display is based at least in part on the raw ambient light signal. In certain embodiments, the method further comprises determining whether an amplitude of the raw ambient light signal is greater than a threshold.

In certain embodiments, the method further comprises determining an amount of sun exposure of the user based at least in part on the second light detector signal. In certain embodiments, the method may further comprise storing a value associated with the second light detector signal in a circular buffer. In certain embodiments, the method further comprises determining whether an amplitude of the second light detector signal is greater than a threshold. In certain embodiments, modifying the brightness level of the electronic display comprises adjusting the brightness level from a first state to a second state. For example, the first state may correspond to a low-light mode and the second state may correspond to a high-light mode.

The method may further include determining one or more physiological characteristics of the user, adjusting one or more illumination parameters of the light source based on the determined one or more physiological characteristics and adjusting one or more reception parameters of the light detector based on the determined one or more physiological characteristics.

In some implementations, the present disclosure relates to a biometric monitoring device comprising a physiological metric monitor module including a light source and a light detector associated with a back side of the biometric monitoring device, the physiological metric monitor module being configured to generate a physiological metric signal when the light source is turned on, and control circuitry configured to determine an amount of ambient light present using the light detector associated with the back side of the biometric monitoring device when the light source is turned off.

In certain embodiments, the biometric monitoring device further comprises an electronic display associated with a front side of the biometric monitoring device, wherein the control circuitry is further configured to adjust a brightness level setting of the electronic display based at least in part on the determined amount of ambient light. The physiological metric monitor module may be further configured to generate the physiological metric signal when the light source is turned off.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

Figure 1:
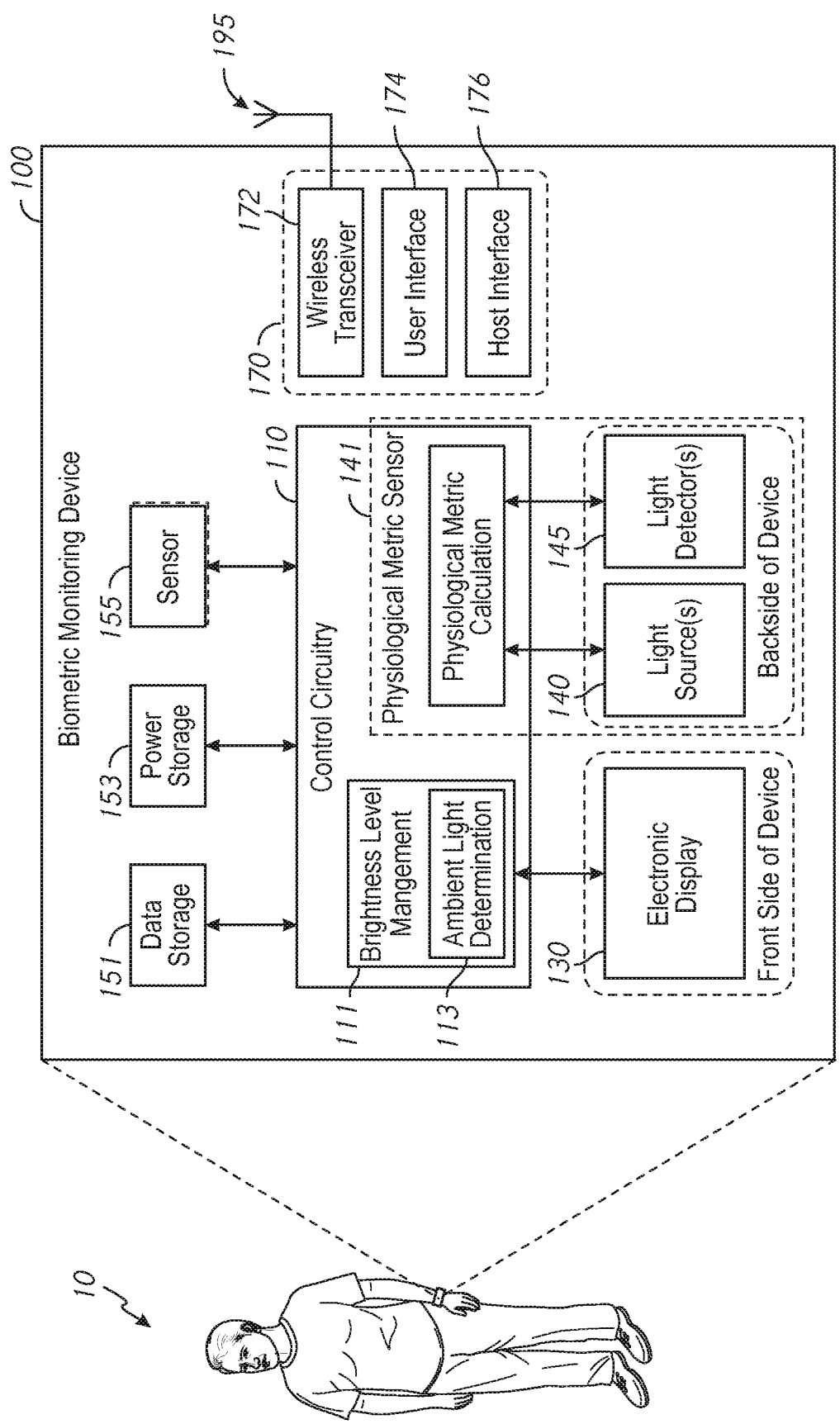
FIG. 1 is a block diagram illustrating an embodiment of a biometric monitoring device according to one or more embodiments.

The headings provided herein are for convenience only and do not necessarily affect the scope or meaning of the claimed invention. Like reference numbers and designations in the various drawings may or may not indicate like elements.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

Biometric monitoring devices, including wrist-worn biometric monitoring devices, can include display screens powered by an internal power source. Due to power and/or visibility considerations, it may be desirable for the brightness setting of the display screen to be adjusted from time to time. For example, when ambient light levels are high, it may be desirable for the brightness setting of the display to be at a high level, while when ambient light levels are low, it may be desirable for the brightness setting of the display to be at a lower level in order to save power and/or reduce the visual strain on the user or reduce other effects associated with over-lighting.

In order to make backlight setting adjustment based on ambient lighting, it may be necessary to generate or otherwise determine information indicating the ambient light level. Brightness level settings for electronic displays, as described herein in connection with various embodiments, may be implemented in any suitable or desirable manner. For example, with respect to liquid crystal display (LCD) devices, the brightness level of the display may be controlled using one or more backlighting devices and/or subsystems. Backlighting devices/subsystems may generally direct light to the electronic display from behind the display. In certain devices, display brightness may be achieved at least in part by reflecting environmental ambient light to light the display as an alternative to, or in addition to, providing light from a backlight device/subsystem. For example, certain devices may include an at least partially transparent light guide structure configured to reflect light entering the light guide from side or edge portions thereof towards the display screen. Although certain embodiments disclosed herein may be described in the context of backlighting devices and/or subsystems, it should be understood that display brightness level setting adjustment in accordance with the present disclosure may implement any suitable or desirable lighting mechanism, and that description herein of backlighting brightness level adjustment should be understood to relate to brightness level setting adjustment for non-backlighting devices/subsystems as well.

Ambient light determinations may be made using dedicated ambient light sensors, such as in the form of an outward-facing sensor disposed on or below the display screen of a biometric monitoring device. Dedicated ambient light sensors may provide relatively high fidelity data indicating ambient lighting conditions. Biometric monitoring devices that do not include ambient light sensing functionality may lack the ability to adjust display brightness settings based on ambient lighting conditions, and therefore may necessarily maintain the display brightness at a maximum operational level at all times to account for the brightest expected ambient light conditions, such as direct outdoor sunlight conditions. The inability to intelligently modify the brightness level setting of the display can have an adverse effect on a biometric monitoring device's battery life, among other things. Therefore, dedicated ambient light sensors may be used to adjust the brightness of a display to conserve battery power and/or provide an improved user experience.

Certain embodiments disclosed herein provide for display brightness level setting adjustment, such as backlighting adjustment, without the aid of an outward-facing dedicated ambient light sensor. For example, biometric monitoring devices in accordance with the present disclosure may incorporate one or more existing functional components or modules designed for determining one or more physiological metrics associated with a user (e.g., wearer) of the device, such as a heart rate sensor or the like. Such components/modules may be disposed or associated with an underside/backside of the biometric monitoring device, and may generally not be in direct exposure to a substantial portion of the ambient light that is present when the biometric monitoring device is worn by a user. For example, where the biometric monitoring device is worn on the user's wrist, the physiological metric component(s)/module(s) may be associated with an underside/backside of the device substantially opposite the display and facing the arm of the user. However, certain underside/backside physiological metric sensor devices or subsystems, such as heart rate sensors in accordance with the present disclosure, may nevertheless be configurable to provide signals indicative of ambient lighting conditions through indirect, or reflective, light detection.

Certain embodiments disclosed herein provide for biometric monitoring devices that utilize ambient light readings derivable from a physiological metric sensor, such as a hear rate sensor (e.g., photoplethysmograph sensor) associated with an underside of a wrist-worn device, for adjusting brightness level settings for the device's electronic display. For example, ambient light readings from a backside physiological metric sensor may be converted to a common reference frame for utilization thereof. Ambient light determination using a backside physiological metric sensor may provide relatively more basic ambient light information than may be achievable using a dedicated outward-facing ambient light sensor, but may still provide adequate information from which to make ambient light determinations among a finite set of ambient light level ranges, such as determining whether ambient lighting conditions indicate indoor or outdoor lighting. Therefore, certain embodiments disclosed herein allow for the detection of indoor versus outdoor lighting conditions without a dedicated outward-facing ambient light sensor by leveraging an existing physiological metric sensor, thereby providing savings with respect to power and extended battery life.

Biometric Monitoring

In some implementations, the present disclosure is related to biometric monitoring devices. The term "biometric monitoring device" is used herein according to its broad and ordinary meaning, and may be used in various contexts herein to refer to any type of biometric tracking devices, personal health monitoring devices, portable monitoring devices, portable biometric monitoring devices, or the like. In some embodiments, biometric monitoring devices in accordance with the present disclosure may be wearable devices, such as may be designed to be worn (e.g., continuously) by a person (i.e., "user," "wearer," etc.). When worn, such biometric monitoring devices may be configured to gather data regarding activities performed by the wearer, or regarding the wearer's physiological state. Such data may include data representative of the ambient environment around the wearer or the wearer's interaction with the environment. For example, the data may comprise motion data regarding the wearer's movements, ambient light, ambient noise, air quality, etc., and/or physiological data obtained by measuring various physiological characteristics of the wearer, such as heart rate, perspiration levels, and the like.

In some cases, a biometric monitoring device may leverage other devices external to the biometric monitoring device, such as an external heart rate monitor in the form of an EKG sensor for obtaining heart rate data, or a GPS receiver in a smartphone may be used to obtain position data, for example. In such cases, the biometric monitoring device may communicate with these external devices using wired or wireless communications connections. The concepts disclosed and discussed herein may be applied to both stand-alone biometric monitoring devices as well as biometric monitoring devices that leverage sensors or functionality provided in external devices, e.g., external sensors, sensors or functionality provided by smartphones, etc.

Biometric Monitoring Devices

Systems, devices and/or methods/processes in accordance with the present disclosure may comprise, or be implemented in connection with, a biometric monitoring device Embodiments of the present disclosure may provide biometric monitoring devices configured to adjust electronic display brightness level settings using ambient light information derived from one or more physiological metric sensors associated with an underside/backside of the biometric monitoring device. It is to be understood that while the concepts and discussion included herein are presented in the context of biometric monitoring devices, these concepts may also be applied in other contexts as well if the appropriate hardware is available. For example, some or all of the relevant sensor functionality may be incorporated in one or more external computing devices (e.g., smartphone) communicatively coupled to the biometric monitoring device.

FIG. 1 is a block diagram illustrating an embodiment of a biometric monitoring device 100 in accordance with one or more embodiments disclosed herein. The biometric monitoring device 100 may be worn by a user 10. The biometric monitoring device 100 may include one or more electronic display units or modules 130, such as a touchscreen display, or the like. In certain embodiments, the electronic display 130 may be associated with the front side of the biometric monitoring device 100. For example, in wearable embodiments of the biometric monitoring device 100, the electronic display 130 may be configured to be externally presented to a user viewing the biometric monitoring device 100. In certain embodiments, the electronic display is illuminated using backlighting, or other lighting mechanism, according to a brightness level setting. In certain embodiments, the display 130 is a front-facing organic light emitting diode (OLED) display. Driving the illumination of the electronic display 130 may represent one of the largest power consumers of the biometric monitoring device 100. In certain embodiments, the brightness of the electronic display is modified according to an ambient light determination, which may, in some cases, provide a power savings of approximately 20-30%, or more, with respect to battery life of the device by reducing the power applied to illuminate the display 130 during certain periods.

Front-facing ambient light sensors may have additional hardware/circuitry associated therewith. Furthermore, it may be desirable to provide display screen treatment to accommodate front-facing ambient light sensors, such as a window in the display screen where the display screen is at least partially covered underneath with a dark paint or the like. While certain front-facing displays of biometric monitoring devices may have dedicated ambient light sensors associated therewith, the biometric monitoring device 100 may be configured to make ambient light determinations without a dedicated ambient light sensor, and may instead repurpose ambient-light-related data from a separate back-facing physiological metric sensor 141 (e.g., optical sensor). By leveraging ambient light data generated using a back-facing physiological metric sensor, certain embodiments disclosed here may advantageously provide cost savings and/or reduced device complexity The biometric monitoring device 100 includes control circuitry 110. Although certain modules and/or components are illustrated as part of the control circuitry 110 in the diagram of FIG. 1, it should be understood that control circuitry associated with the biometric monitoring device 100 and/or other components or devices in accordance with the present disclosure may include additional components and/or circuitry, such as one or more of the additional illustrated components of FIG. 1. Furthermore, in certain embodiments, one or more of the illustrated components of the control circuitry 110 may be omitted and/or different than that shown in FIG. 1 and described in association therewith. The term "control circuitry" is used herein according to its broad and ordinary meaning, and may include any combination of software and/or hardware elements, devices or features, which may be implemented in connection with operation of the biometric monitoring device 100. Furthermore, the term "control circuitry" may be used substantially interchangeably in certain contexts herein with one or more of the terms "controller," "integrated circuit," "IC," "application-specific integrated circuit," "ASIC," "controller chip," or the like.

The control circuitry 110 may comprise one or more processors, data storage devices, and/or electrical connections. For example, the control circuitry 110 may comprise one or more processors configured to execute operational code for the biometric monitoring device 100, such as firmware or the like, wherein such code may be stored in one or more data storage devices of the biometric monitoring device 100. In one embodiment, the control circuitry 110 is implemented on an SoC (system on a chip), though those skilled in the art will recognize that other hardware/firmware implementations are possible.

The control circuitry 110 may comprise a brightness level management module 111. The brightness level management module 111 may comprise one or more hardware and/or software components or features configured to control a brightness level setting for the electronic display 130. In certain embodiments, the brightness level management module 111 may comprise ambient light detection functionality, wherein data associated with, or indicative of, ambient lighting conditions of an environment in which the biometric monitoring device 100 is disposed may be used to determine an appropriate or desirable brightness level setting for the electronic display 130.

The control circuitry 110 may further comprise an optical physiological metric sensor 141 that includes: a physiological metric calculation module 115, which may be configured to determine one or more physiological metrics associated with the user 10 of the biometric monitoring device 100; light source(s) 140 located on the backside of the device, which may be configured to emit light in one or more wavelengths; and light detector(s) 145 located on the backside of the device, which may be configured to detect light reflected from the tissue of the user 10. As is discussed below, the optical physiological metric sensor 141 may include circuitry configured to detect ambient lighting conditions using the light detector(s) 145 in order to subtract or cancel the unwanted ambient light from the optical readings of the light detector(s) 145. For example, ambient light reflected into the light detector(s) 145 may distort the sensor signal that is designed to generate readings indicative of light originating from the light sources(s) 140.

The physiological metric calculation module 115 may be configured to generate physiological metric data based on readings from one or more light detectors 145, and/or one or more other sensor devices 155. The light detectors 145 may be configured to detect light generated by one or more light sources 140, as well as ambient light to which the detector 145 is exposed.

As mentioned above, the light sources 140 and/or light detector 145 may be associated with the backside of the biometric monitoring device 100. For example, in a wearable configuration of the biometric monitoring device 100, whereas the electronic display may be generally outward-facing, the light sources 140 and/or light detectors 145 may be physically connected to and/or associated with an underside (i.e., backside) of the biometric monitoring device that may be generally skin-facing when worn by the user 10, such as on a wrist, arm, leg, or other appendage or body part of the user 10.

In operation, in certain embodiments, the physiological metric calculation module 115 may be configured to activate the light source(s) 140 and/or otherwise cause the light source(s) 140 to generate or direct the light in a direction towards the tissue or body of the user 10, wherein the light detector(s) 145 detects light reflecting back from the user. Such detected reflected light from the user may be used to determine one or more physiological metrics associated with the user 10, such as heart rate, blood oxygenation, or the like. To the extent that the reflected light detected by the light detector 145 includes direct or reflected ambient light in addition to the light generated by the light source(s) 140, such additional light may undesirably obfuscate the determination of the relevant physiological metric(s). Therefore, in certain embodiments, the physiological metric calculation module 115 may be configured to at least partially cancel out the detected ambient light in order to provide more accurate physiological metric calculation. In certain embodiments, the physiological metric calculation module 115 may cancel out the ambient light at least in part by utilizing a reading from the light detector 145 during a period of time in which the light sources 140 are not activated in order to obtain a reading indicative of the ambient light exposed to the light detector 145. In order to promote correspondence between the ambient light detected during the period in which the light sources 140 are not active and the period in which the light sources 140 are active, such periods may advantageously be temporally close to one another.

The biometric monitoring device may further comprise one or more data storage modules 151, which may include any suitable or desirable type of data storage, such as solid-state memory, which may be volatile or non-volatile. In some embodiments the memory is non-transitory. Solid-state memory of the biometric monitoring device 100 may comprise any of a wide variety of technologies, such as flash integrated circuits, Phase Change Memory (PC-RAM or PRAM), Programmable Metallization Cell RAM (PMC-RAM or PMCm), Ovonic Unified Memory (OUM), Resistance RAM (RRAM), NAND memory, NOR memory, EEPROM, Ferroelectric Memory (FeRAM), MRAM, or other discrete NVM (non-volatile solid-state memory) chips. The data storage 151 may be used to store system data, such as operating system data and/or system configurations or parameters. The biometric monitoring device 100 may further comprise data storage utilized as a buffer and/or cache memory for operational use by the control circuitry 110.

The biometric monitoring device 100 further comprises power storage 153, which may comprise a rechargeable battery, one or more capacitors, or other charge-holding device(s). The power stored by the power storage module 153 may be utilized by the control circuitry 110 for operation of the biometric monitoring device 100, such as for powering the light sources 140 and/or display 130. The power storage module 153 may receive power over the host interface 176 or through other means.

The biometric monitoring device 100 may further comprise one or more connectivity components 170, which may include, for example, a wireless transceiver 172. The wireless transceiver 172 may be communicatively coupled to one or more antenna devices 195, which may be configured to wirelessly transmit/receive data and/or power signals to/from the biometric monitoring device. For example, the wireless transceiver 172 may be utilized to communicate data and/or power between the biometric monitoring device 100 and an external host system (not shown), which may be configured to interface with the biometric monitoring device 100. In certain embodiments, the biometric monitoring device 100 may comprise additional host interface circuitry and/or components 176, such as wired interface components for communicatively coupling with a host device or system to receive data and/or power therefrom and/or transmit data thereto.

The connectivity circuitry 170 may further comprise user interface components 174 for receiving user input. For example, the user interface 174 may be associated with the electronic display 130, wherein the electronic display is a touchscreen display configured to receive user input from user contact therewith. The user interface module 174 may further comprise one or more buttons or other input components or features.

The connectivity circuitry 170 may further comprise the host interface 176, which may be, for example, an interface for communicating with a host device or system (not shown) over a wired or wireless connection. The host interface 176 may be associated with any suitable or desirable communication protocol and/or physical connector, such as Universal Serial Bus (USB), Micro-USB, WiFi, Bluetooth, FireWire, PCIe, or the like. For wireless connections, the host interface 176 may be incorporated with the wireless transceiver 172.

The biometric monitoring device 100 may be configured to implement intelligent brightness level setting adjustment for the electronic display based on data generated by the physiological metric sensor 141. Although certain functional modules and components are illustrated and described herein, it should be understood that ambient light sensing and/or brightness level setting adjustment functionality in accordance with the present disclosure may be implemented using a number of different approaches. For example, in some implementations the control circuitry 110 may comprise one or more processors controlled by computer-executable instructions stored in non-transitory memory (e.g., a non-transitory storage medium) so as to provide functionality such as is described herein. In other implementations, such functionality may be provided in the form of one or more specially-designed electrical circuits. In some implementations, such functionality may be provided by one or more processors controlled by computer-executable instructions stored in a memory coupled with one or more specially-designed electrical circuits. Various examples of hardware that may be used to implement the concepts outlined herein include, but are not limited to, application specific integrated circuits (ASICs), field-programmable gate arrays (FPGAs), and general-purpose microprocessors coupled with memory that stores executable instructions for controlling the general-purpose microprocessors.

Standalone biometric monitoring devices may be implemented in a number of form factors and may be designed to be worn in a variety of ways. In some implementations, a biometric monitoring device may be designed to be insertable into a wearable case or into one or more of multiple different wearable cases (e.g., a wristband case, a belt-clip case, a pendant case, a case configured to be attached to a piece of exercise equipment such as a bicycle, etc.). Certain such implementations are described in more detail in, for example, U.S. Pub. No. 2014/0180019, published on Jun. 26, 2014, which is hereby incorporated by reference for such purpose. In other implementations, a biometric monitoring device may be designed to be worn in limited manners, such as a biometric monitoring device that is integrated into a wristband in a non-removable manner and may be intended to be worn specifically on a person's wrist (or perhaps ankle).

Figure 2:
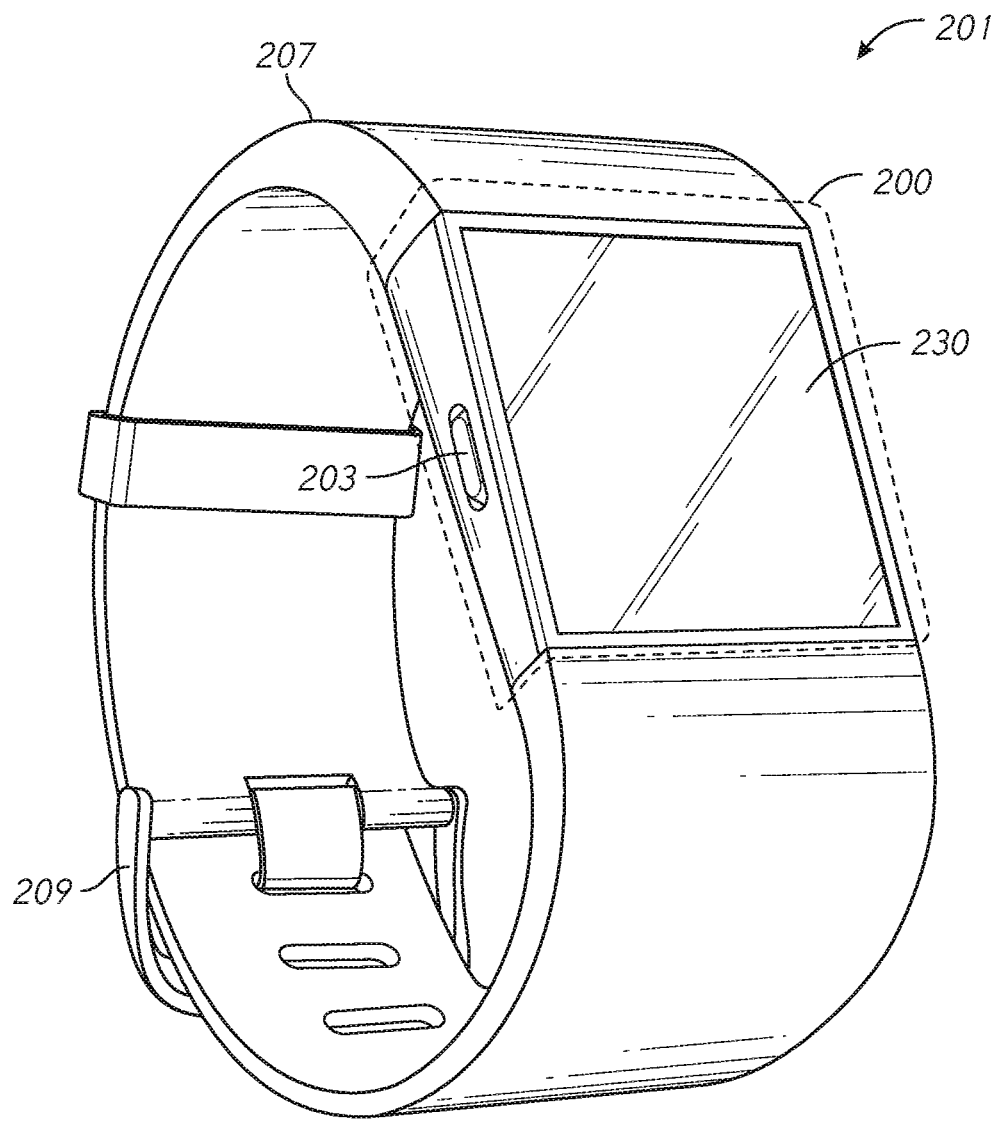
FIG. 2 provides a perspective front and side view of a wearable biometric monitoring device according to one or more embodiments.

Wearable biometric monitoring devices according to embodiments and implementations described herein may have shapes and sizes adapted for coupling to (e.g., secured to, worn, borne by, etc.) the body or clothing of a user. An example of a wearable biometric monitoring device 201 is shown in FIG. 2. FIG. 2 shows perspective front and side views of the wearable biometric monitoring device 201. The wearable biometric monitoring device 201 includes both a biometric monitoring device 200, as well as a band portion 207. In certain embodiments, the band portion 207 includes first and second portions that may be connected by a clasp portion 209. The biometric monitoring device portion 200 may be insertable, and may have any suitable or desirable dimensions. Wearable biometric monitoring devices may generally be relatively small in size so as to be unobtrusive for the wearer. The biometric monitoring device 200 may be designed to be able to be worn without discomfort for long periods of time and to not interfere with normal daily activity.

The electronic display 230 may comprise any type of electronic display known in the art. For example, the display 230 may be a liquid crystal display (LCD) or organic light emitting diode (OLED) display, such as a transmissive LCD or OLED display. The electronic display 230 may be configured to provide brightness, contrast, and/or color saturation features according to display settings maintained by control circuitry and/or other internal components/circuitry of the biometric monitoring device 200. The brightness of the display 230 may be implemented through the use of a brightness component. In certain embodiments, the brightness component can include backlighting mechanisms, which may comprise one or more internal light sources positioned behind the display screen to provide illumination thereto. In some embodiments, the backlighting component comprises one or more light-emitting diodes (LEDs) (e.g., white LEDs). The terms "backlight," "backlighting," "backlighting component," "backlighting mechanism," "backlighting subsystem," and "backlighting module" are used herein according to their broad and ordinary meanings, and may be used to refer generally to one or more lighting devices that may be activated to illuminate a display or otherwise make a display more visible to a user, and/or to circuitry (hardware and/or code) for managing or controlling a brightness setting of an electronic display. In some contexts, the above-recited terms may be used to refer to an actual brightness, or quantity of light, produced or generated by an electronic display. In other contexts, the above-recited terms may be used to refer to a separate lighting component that produces or generates ambient light (reflective light or illumination), transmissive light, or some combination thereof (transflective light or illumination) with respect to the electronic display. By adjusting the brightness of the electronic display 130, the brightness level management module 111 may provide power savings.

Figure 3:
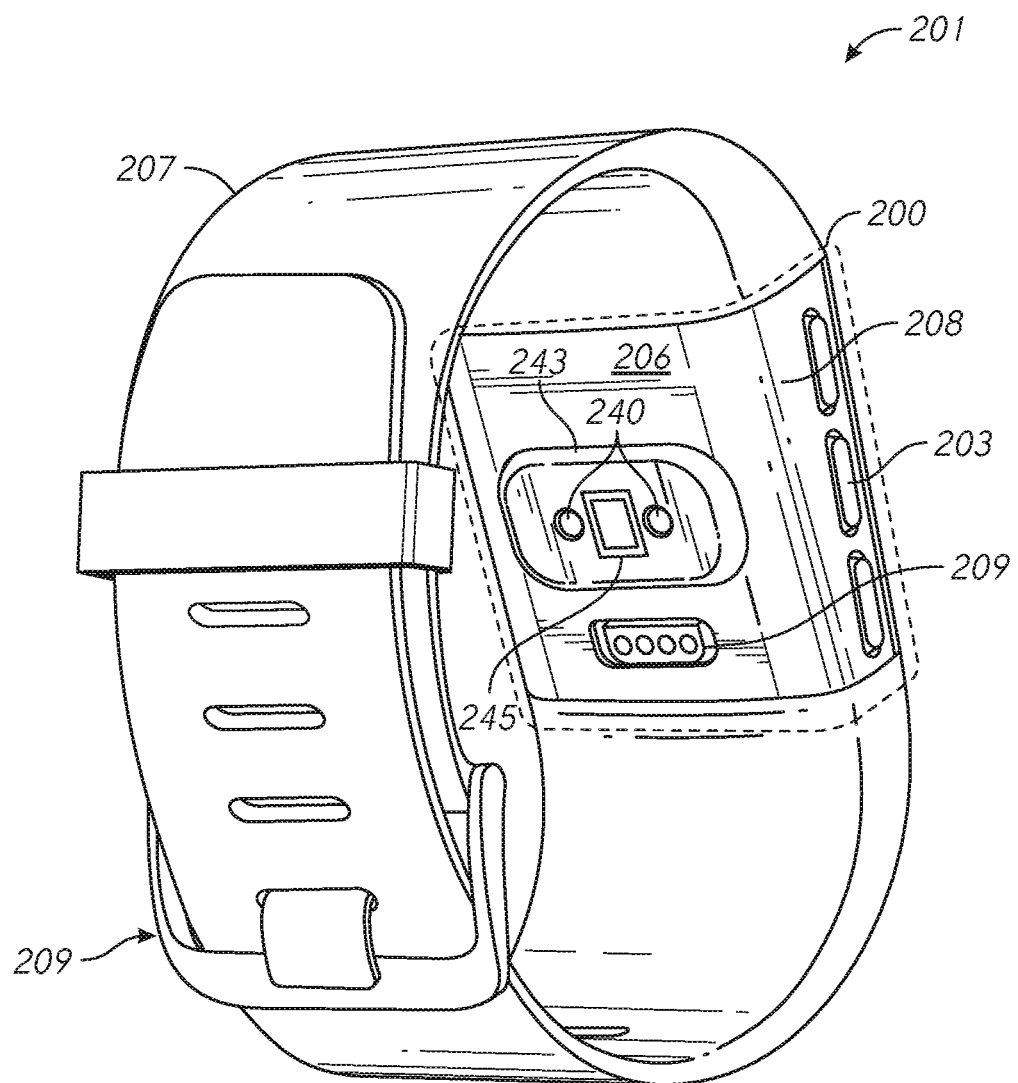
FIG. 3 provides a perspective back and side view of the wearable biometric monitoring device of FIG. 2 according to one or more embodiments.

The power consumption associated with the display illumination component can be relatively high in some embodiments, particularly when implementing a maximum brightness level. Although a maximum brightness level setting may be desirable in outdoor daylight conditions, certain embodiments of the present disclosure advantageously provide for intelligent brightness level adjustment, which may provide power savings when the brightness level is set to a reduced brightness state, such as when the ambient light levels are below outdoor daylight levels. In some implementations, such power savings may be achieved without the use of dedicated ambient light sensors on, or associated with, the outward-facing surface of an electronic display FIG. 3 is a perspective back and side view of the wearable biometric monitoring device 201 of FIG. 2. The wearable biometric monitoring device 201 comprises a band portion 207, which may be configured to be latched or secured about a user's arm or other appendage via a securement mechanism of any suitable or desirable type. For example, the band 207 may be secured using a hook and loop clasp component 209. In certain embodiments, the band 207 is designed with shape memory to promote wrapping around the user's arm.

The wearable biometric monitoring device 201 includes a biometric monitoring device component 200, which may be at least partially secured to the band 207. The view of FIG. 3 shows a backside 206 (also referred to herein as the "underside") of the biometric monitoring device 200, which may generally face and/or contact skin or clothing associated with the user's arm, for example. The terms "backside" and "underside" are used herein according to their broad and ordinary meaning, and may be used in certain contexts to refer to a side, panel, region, component, portion and/or surface of a biometric monitoring device that is positioned and/or disposed substantially opposite to a user display screen, whether exposed externally of the device, or at least partially internal to an electronics package or housing of the device.

The biometric monitoring device 200 may include one or more buttons 203, which may provide a mechanism for user input. The biometric monitoring device 200 may further comprise a device housing, which may comprise one or more of steel, aluminum, plastic, and/or other rigid structure. The housing 208 may serve to protect the biometric monitoring device 200 and/or internal electronics/components associated therewith from physical damage and/or debris. In certain embodiments, the housing 208 is at least partially waterproof.

The backside 206 of the biometric monitoring device 200 may have an optical physiological metric sensor 243 associated therewith, which may comprise one or more sensor components, such as one or more light sources 240 and/or light detectors 245, the collection of which may represent an example of the optical physiological metric sensor 141 of FIG. 1. In certain embodiments, the optical physiological metric sensor 243 comprises a protrusion form protruding from the back surface of the biometric monitoring device 200. The sensor components may be used to determine one or more physiological metrics of a user wearing the wearable biometric monitoring device 201. For example, the optical physiological sensor components associated with the sensor 243 may be configured to provide readings used to determine heart rate (e.g., in beats-per-minute (BPM)), blood oxygenation (e.g., $SpO_2$), blood pressure, or other metric. In certain embodiments, the biometric monitoring device 200 further includes an electrical charger mating recess 209.

As the sensor 243 may be present and configured to detect ambient light in connection with heart-rate-related optical measurements, or other type of physiological parameter measurement, certain embodiments disclosed herein may advantageously leverage or repurpose the ambient light signal(s) associated with the sensor 243 for the purpose of making a determination relating to ambient light conditions. For example, ambient light determinations may advantageously indicate whether the biometric monitoring device 200 is indoors or outdoors.

Generally, lighting conditions outdoors may be substantially greater with respect to luminous flux than lighting conditions indoors. When the sensor 243 is used to take optical readings of light that is reflected back into the sensor from the user's tissue/blood, such readings may generally comprise a combination of ambient light and reflected light from the light sources 240. Therefore, in order to obtain a reading that is not influenced by the ambient light, it may be desirable to cancel the ambient light from the sensor signal (s)/data. In order to achieve such cancellation, the sensor 243 may implement a phase during which the light sensor(s) 245 is/are read without the light source(s) being active, such that detected light is substantially wholly attributable to ambient light. The light source(s) 140 may then be activated, wherein the resulting light detection is processed in such a way as to at least partially subtract the ambient light read during the off phase, thereby providing a signal/data that is estimated to be attributable substantially wholly to the light generated by the device 200. In certain embodiments, the ambient light readings used to cancel ambient light may be obtained during a phase in which the light source(s) are actively emitting light. For example, in one implementation, the sensor 243 may be configured to detect ambient light in a first phase in which the light emitter(s) of the sensor 243 are turned off, and again in a second phase in which the light emitter(s) are turned on. For example, in the second phase, the light emitter(s) may be driven at a relatively low level. Additional embodiments and details relating to ambient light detection are disclosed in U.S. patent application Ser. No. 15/223,589, entitled "Circuits and Methods for Photoplethysmographic Sensor," filed on Jul. 29, 2016, the disclosure of which is hereby explicitly incorporated by reference in its entirety.

Because the light detector 245 is disposed on the backside of the device 200, which is generally at least partially shielded from direct light when worn by the user, the ambient light reading from the light detector 245 may not be as precise as certain other ambient light sensor embodiments. However, when making a simple binary determination of whether the device is indoors or outdoors, the relatively crude ambient light information may nevertheless be sufficient. Therefore, it may not be necessary to implement a forward-facing ambient light sensor; rather, relatively basic assessment of ambient light conditions may be adequate, and dynamic adjustment of display brightness level may be unnecessary. When it is determined that the biometric monitoring device 200 is outdoors, the device may implement a full brightness setting or mode, whereas a less bright setting or mode may be used where indoor lighting is detected.

Although the sensor 243 is illustrated as comprising a protrusion form certain figures herein, it should be understood that backside sensor modules in accordance with the present disclosure may or may not be associated with a protrusion form. In certain embodiments, the protrusion form on the backside of the device may be designed to engage the skin of the user with more force than the surrounding device body. In certain embodiments, an optical window or light-transmissive structure may be incorporated in a portion of the protrusion 243. The light emitter(s) 240 and/or detector(s) 245 of the sensor module 243 may be disposed or arranged in the protrusion 243 near the window or light-transmissive structure. As such, when attached to the user's body, the window portion of the protrusion 243 of the biometric monitoring device 200 may engage the user's skin with more force than the surrounding device body, thereby providing a more secure physical coupling between the user's skin and the optical window. That is, the protrusion 243 may cause sustained contact between the biometric monitoring device and the user's skin that may reduce the amount of stray light measured by the photodetector 245, decrease relative motion between the biometric monitoring device 200 and the user, and/or provide improved local pressure to the user's skin, some or all of which may increase the quality of the cardiac signal of interest generated by the sensor module. Notably, the protrusion 243 may contain other sensors that benefit from close proximity and/or secure contact to the user's skin. These may be included in addition to or in lieu of a heart rate sensor and may include sensors such as a skin temperature sensor (e.g., noncontact thermopile that utilizes the optical window or thermistor joined with thermal epoxy to the outer surface of the protrusion), pulse oximeter, blood pressure sensor, EMG, or galvanic skin response (GSR) sensor.

In certain embodiments, a portion of the backside of the biometric monitoring device 200 may include a friction-enhancing mechanism or material. For example, the backside of the biometric monitoring device 200 may include a plurality of raised or depressed regions or portions (for example, small bumps, ridges, grooves, and/or divots). Moreover, a friction enhancing material (for example, a gel-like material such as silicone or other elastomeric material) may be disposed on the skin-side, while may further improve user comfort and/or prevent stray light from entering. The use of a protrusion and/or friction may improve measurement accuracy of data acquisition corresponding to certain parameters (e.g., heart rate, heart rate variability, galvanic skin response, skin temperature, skin coloration, heat flux, blood pressure, blood glucose, etc.) by reducing motion of the biometric monitoring device 200 (and thus of the sensor) relative to the user's skin during operation, particularly while the user is in motion.

Some or all of the backside housing 208 of the biometric monitoring device 200 may comprise a metal material (for example, steel, stainless steel, aluminum, magnesium, or titanium). Such a configuration may provide desirable structural rigidity. In certain embodiments, the housing 208 is at least partially ferrous (for example, a grade of stainless steel that is ferrous). In such embodiments, the biometric monitoring device 200 may interconnect with a charger via a connector that secures itself to the biometric monitoring device using magnets that couple to the ferrous material. The biometric monitoring device 200 may also engage a dock or docking station, using such magnetic properties, to facilitate data and/or power transfer. Moreover, such a housing may provide enhanced electromagnetic shielding that may enhance the integrity and/or reliability of the optical physiological sensor (e.g., heart rate sensor) and the physiological metric data acquisition process/operation.

The biometric monitoring device 200 may be configured to collect one or more types of physiological and/or environmental data from embedded sensors and/or external devices and communicate or relay such information to other devices, including devices capable of serving as an Internet-accessible data sources, thus permitting the collected data to be viewed, for example, using a web browser or network-based application. For example, while the user is wearing the biometric monitoring device 200, the biometric monitoring device 200 may calculate and store the user's step count using one or more biometric sensors. The biometric monitoring device may then transmit data representative of the user's step count to an account on a web service, computer, mobile phone, or health station where the data may be stored, processed, and visualized by the user. Indeed, the biometric monitoring device 200 may measure or calculate a plurality of other physiological metrics in addition to, or in place of, the user's step count. These include, but are not limited to, energy expenditure, e.g., calorie burn, floors climbed and/or descended, heart rate, heart rate variability, heart rate recovery, location and/or heading, e.g., through GPS or a similar system, elevation, ambulatory speed and/or distance traveled, swimming lap count, swimming stroke type and count detected, bicycle distance and/or speed, blood pressure, blood glucose, skin conduction, skin and/or body temperature, muscle state measured via electromyography, brain activity as measured by electroencephalography, weight, body fat, caloric intake, nutritional intake from food, medication intake, sleep periods, e.g., clock time, sleep phases, sleep quality and/or duration, pH levels, hydration levels, respiration rate, and other physiological metrics.

The biometric monitoring device 200 may also measure or calculate metrics related to the environment around the user such as barometric pressure, weather conditions (e.g., temperature, humidity, pollen count, air quality, rain/snow conditions, wind speed), light exposure (e.g., ambient light, UV light exposure, time and/or duration spent in darkness), noise exposure, radiation exposure, and magnetic field. Furthermore, the biometric monitoring device 200 or the system collating the data streams from the biometric monitoring device may calculate metrics derived from such data. For example, the device or system may calculate the user's stress and/or relaxation levels through a combination of heart rate variability, skin conduction, noise pollution, and sleep quality. In another example, the biometric monitoring device 200 may determine the efficacy of a medical intervention, e.g., medication, through the combination of medication intake, sleep data, and/or activity data. In yet another example, the biometric monitoring device or system may determine the efficacy of an allergy medication through the combination of pollen data, medication intake, sleep and/or activity data. These examples are provided for illustration only and are not intended to be limiting or exhaustive. Further embodiments and implementations of sensor devices may be found in U.S. Pat. No. 9,167,991, titled "Portable Biometric Monitoring Devices and Methods of Operating Same" filed Jun. 8, 2011, which is hereby incorporated herein by reference in its entirety.

Physiological Metric Sensor Module

An optical physiological metric sensor such as photoplethysmography (PPG) sensors may generally utilize light sensors and/or detectors to obtain a volumetric measurement relating to pulsatile blood flow in the body. PPG information may be obtained illuminating the skin of a subject and measuring changes in light absorption. A PPG sensor can be designed to monitor the perfusion of blood to the dermis and/or subcutaneous tissue of the skin. PPG data may be determined using a wrist-worn biometric monitoring device based on the pumping of blood to the periphery during each cardiac cycle. While the pressure pulse may be somewhat damped by the time it reaches the skin, it may nevertheless be enough to distend the arteries and/or arterioles in the subcutaneous tissue of the wearer of the biometric monitoring device. The change in volume caused by the pressure pulse may be detected by illuminating the skin with the light from one or more light source (e.g., light-emitting diodes (LEDs)) and then measuring the amount of light either transmitted or reflected to one or more light sensors (e.g., photodiode(s)). In certain embodiments, as blood flow to the skin can be modulated by various other physiological systems, the PPG sensor may further be used to monitor breathing, hypovolemia, and/or other circulatory conditions.

PPG readings can be used to determine heart rate, SpO2, and the like. While PPGs can be obtained in certain systems using transmissive absorption, with respect certain wrist-worn biometric monitoring devices disclosed herein, PPG information may be obtained using reflective absorption. For PPG signals, the DC component of the signal may be attributable to the bulk absorption of the skin tissue, while the AC component may be attributable to variation in blood volume in the skin caused by the pressure pulse of the cardiac cycle. Generally, the height of the AC component of the PPG signal may be proportional to the pulse pressure, which is the difference between the systolic and diastolic pressure in the arteries. Although certain embodiments are presented herein in the context of PPG sensors, it should be understood that ambient light data for electronic display brightness level management in accordance with the present disclosure may incorporate ambient light signals from any suitable or desirable physiological metric sensor.

Figure 4:
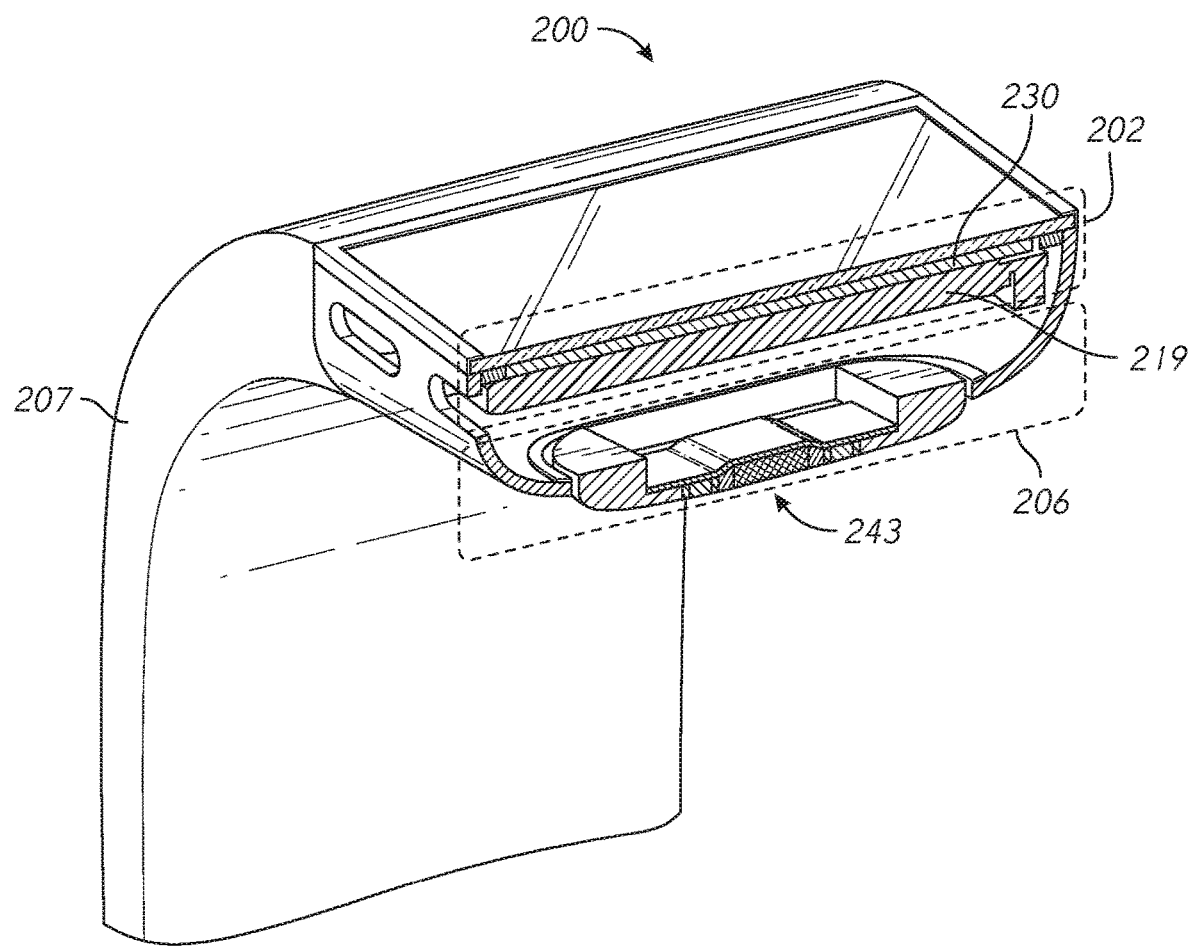
FIG. 4 provides a cross-sectional view of the biometric monitoring device of FIG. 2 according to one or more embodiments.

FIG. 4 shows a cross-sectional view of the biometric monitoring device 200 of FIGS. 2 and 3 according to one or more embodiments, which is attached to a band portion 207. The diagram of FIG. 4 shows a cross-section of the sensor protrusion 243 shown in FIG. 3, example embodiments of which are illustrated in further detail in FIGS. 5 and 6 and described below. Certain electronic/circuitry components of the biometric monitoring device 200 may be mounted to or otherwise associated with a controller board 219, which may comprise, for example, one or more printed circuit boards (PCBs). The controller board 219 may comprise controller circuitry operating the biometric monitoring device 200. In certain embodiments, the sensor module 243 may be configured to generate sensor signals and provide such sensor signals to the controller board circuitry for processing thereof. For example, the controller circuitry 110 of FIG. 1 and described above may be implemented at least in part as a controller board like that shown in FIG. 4.

The sensor protrusion 243 and/or associated components may be part of a backside, or underside, 206 of the biometric monitoring device 200. The backside 206 of the biometric monitoring device 200 may be positioned substantially opposite a front side 202, which may be associated with an electronic display 230, which may be illuminated using backlighting or other lighting mechanism according to a brightness level setting managed at least in part by the controller board 219 as described herein.

Figure 5:
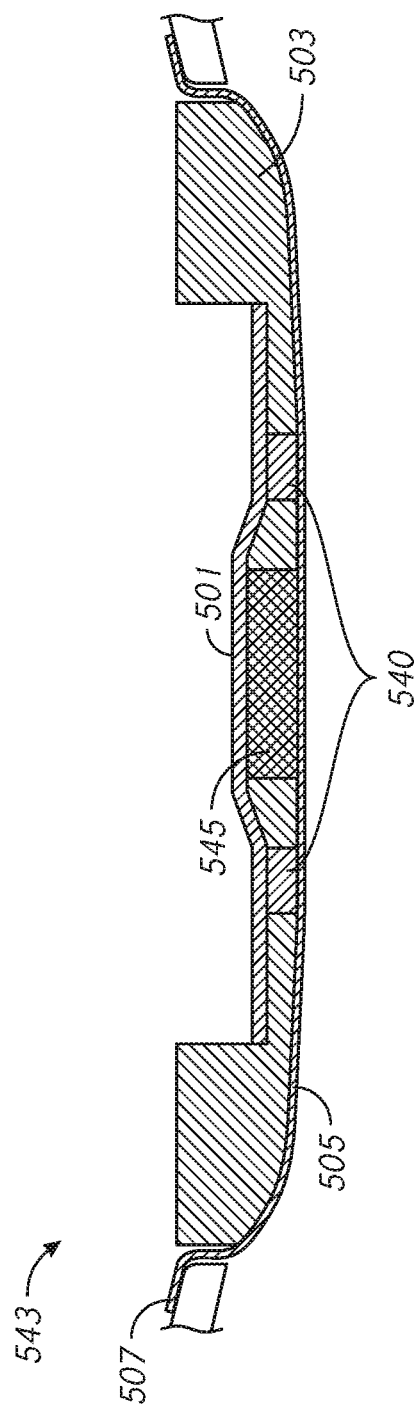
FIG. 5 provides a cross sectional view of a sensor protrusion of a biometric monitoring device according to one or more embodiments.

In some implementations, the sensor protrusion 243 may comprise an optical sensor, which may be positioned on the backside 206 (e.g., skin-side) of the device and arranged or positioned to reduce or minimize the distance between the light source(s) and/or the associated detector(s) and the skin of the user. FIG. 5 shows a cross-sectional view of a backside sensor module for a biometric monitoring device according to one or more embodiments. For example, the sensor module 543 may be part of a sensor protrusion like that shown in FIG. 4 and described above. In FIG. 5, two light sources 540 (e.g., LEDs) are placed on either side of a photodetector 545 to enable photoplethysmograph (PPG) sensing in accordance with the present disclosure. A light-blocking material 503 may be placed between the light sources 540 and the photodetector 545 to at least partially prevent light from the light sources 540 from reaching the photodetector 545 without first exiting the housing of the biometric monitoring device. In certain embodiments, a flexible transparent layer 505 may be placed on the lower surface of the sensor module 543 to form a seal. The transparent layer 505 may further serve certain other functions, such as preventing liquid from entering the device where the light sources 540 or photodetectors 545 are placed. The transparent layer 505 may be formed through in-mold labeling, or other process. In certain embodiments, the light sources 540 and/or photodetector 545 may be placed on a flexible circuit board 501.

The configuration of FIG. 5 may improve the efficiency of light flux coupling between the components of the optical sensor module 543 and the user's body. For example, in one embodiment, the light source(s) 540 and/or associated detector(s) 545 may be disposed on a flexible or pliable substrate. Such flexibility may allow the backside of the biometric monitoring device, which may be made from a compliant material, to at least partially conform to the shape of the body part (for example, the user's wrist, arm, ankle, and/or leg) to which the biometric monitoring device is coupled to or attached during normal operation, such that the light source(s) 540 and/or associated detector(s) 545 are close to the skin of the user (i.e., with little or no gap between the skin-side of the device and the adjacent surface of the skin of the user.

Figure 6:
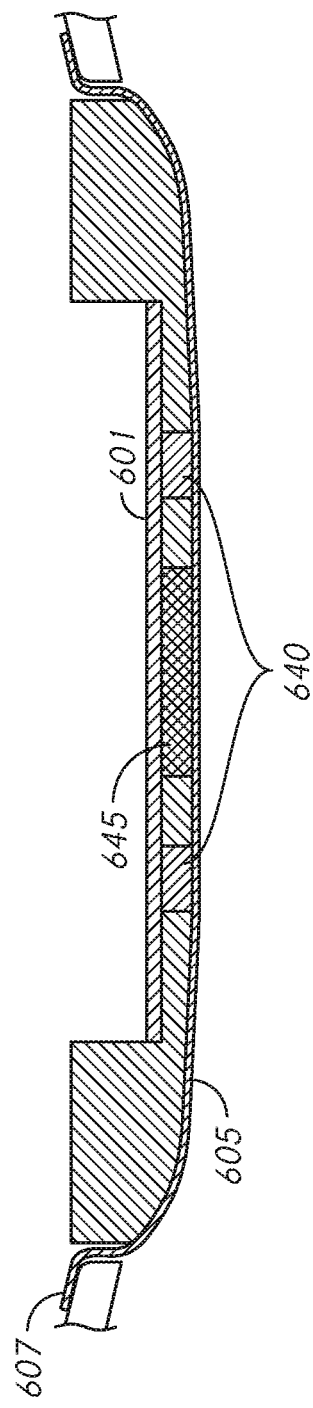
FIG. 6 provides a cross sectional view of a sensor protrusion of a biometric monitoring device according to one or more embodiments.

FIG. 6 depicts a cross-sectional view of a sensor protrusion 643 of an example wearable biometric monitoring device. In the embodiment of FIG. 6, one or more of the light sources 640 and photo detector(s) 645 may be disposed on a flat and/or rigid circuit board (PCB).

Figure 7A:
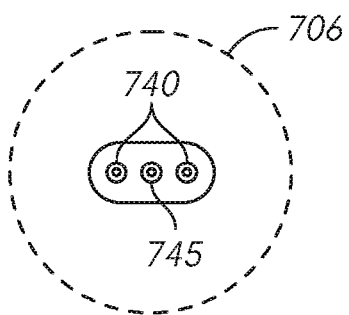
FIG. 7A illustrates photoplethysmograph (PPG) sensor module according to one or more embodiments.
Figure 7B:
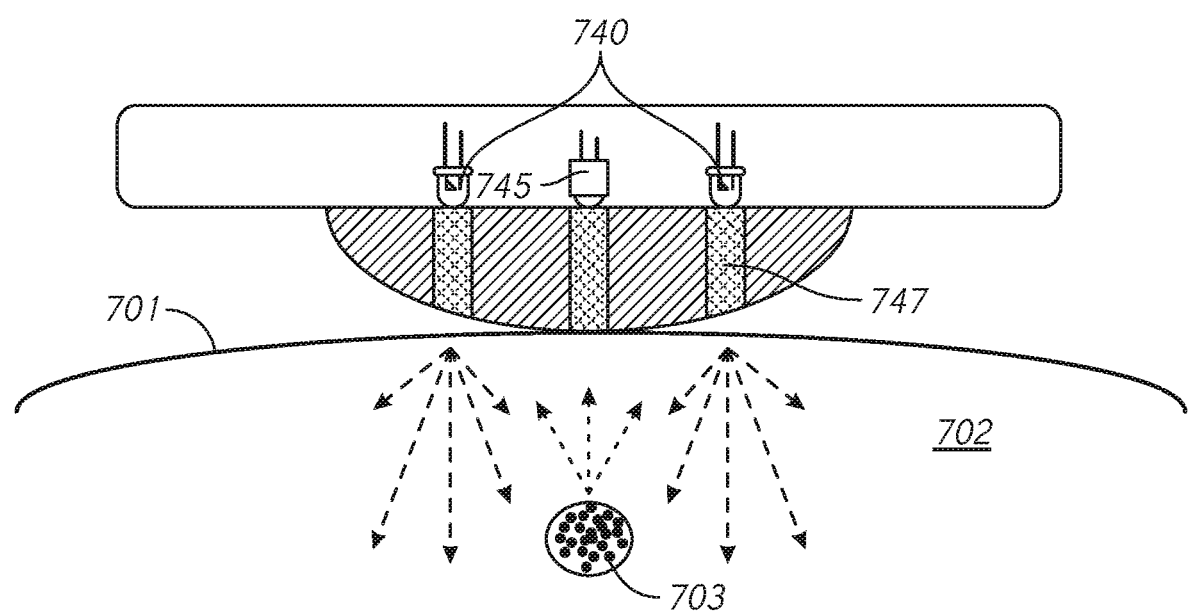
FIGS. 7B and 7C illustrate examples of a PPG sensor having a photodetector and two LED light sources according to one or more embodiments.
Figure 7C:
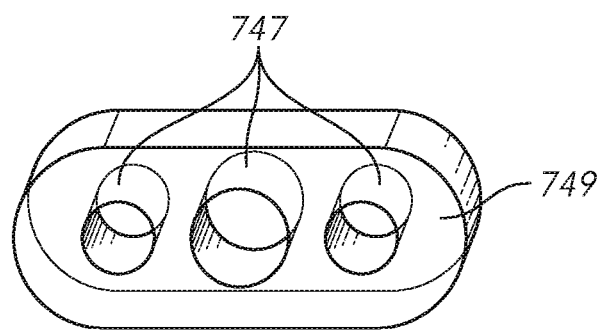

FIGS. 7A-7C provide diagrams of physiological metric sensor components according to certain embodiments. Physiological metric sensor modules, such as optical sensor modules, in biometric monitoring devices of the present disclosure may employ light pipes 747 or other light-transmissive structures to facilitate transmission of light from light sources 740 to a user's body 702 and skin 701. In this regard, in some embodiments, light may be directed from the light source(s) 740 to the skin 701 of the user through such light pipes 747 or other light-transmissive structures. Scattered light from the user's body may be directed back to optical circuitry in the biometric monitoring device through the same or similar structures. Indeed, the light-transmissive structures 747 may employ a material and/or optical design to facilitate low light loss (for example, the light-transmissive structures 747 may include a lens to facilitate light collection, and portions of the light-transmissive structures may be coated with or adjacent to reflective materials to promote internal reflection of light within the light-transmissive structures), thereby improving the signal-to-noise-ratio of the photo detector(s) 745 and/or facilitating reduced power consumption of the light source(s) 740 and/or light detector(s) 745. In some embodiments, the light pipes 747 or other light-transmissive structures may include a material that selectively transmits light having one or more specific or predetermined wavelengths with higher efficiency than others, thereby acting as a bandpass filter. Such a bandpass filter may be tuned to improve the signal of a specific physiological data type. For example, in one embodiment, an In-Mold-Labeling (IML) light-transmissive structure may be implemented, wherein the light-transmissive structure uses a material with predetermined or desired optical characteristics to create a specific bandpass characteristic, for example, so as to pass infrared light with greater efficiency than light of other wavelengths (for example, light having a wavelength in human visible spectrum). In another embodiment, a biometric monitoring device may employ a light-transmissive structure having an optically opaque portion (including certain optical properties) and an optically-transparent portion (including optical properties different from the optically-opaque portion). Such a light-transmissive structure may be provided via a double-shot or two-step molding process wherein optically opaque material and optically transparent material are separately injected into a mold. A biometric monitoring device implementing such a light-transmissive structure may include different light transmissivity properties for different wavelengths depending on the direction of light travel through the light-transmissive structure. For example, in one embodiment, the optically-opaque material may be reflective to a specific wavelength range so as to more efficiently transport light from the user's body back to the light detector (which may be of a different wavelength(s) relative to the wavelength(s) of the emitted light).

In certain embodiments, reflective structures may be placed in the field of view of the light emitter(s) 740 and/or light detector(s) 745. For example, the sides of the light transmission channels may be at least partially covered in a reflective material (e.g., chromed) to facilitate light transmission. The reflective material may increase the efficiency with which the light is transported to the skin 701 from the light source(s) 740 and then from the skin back into the detector(s) 745. The reflectively-coated channel may be filled in with an optical epoxy or other transparent material to prevent liquid from entering the device body while still allowing light to be transmitted with low transmission loss.

In certain embodiments, light-transmissive channels/structures 747 may include a mask consisting of an opaque material that limits the aperture of one, some, or all of the light source(s) and/or detector(s). In this way, the light-transmissive structures 747 may selectively define a preferential volume of the user's body that light is emitted into and/or detected from. Notably, other mask configurations may be employed or implemented in connection with the concepts described and/or illustrated herein that improve the photoplethysmography signal and which are implemented in connection with the concepts described and/or illustrated herein are intended to fall within the scope of the present disclosure.

In certain embodiments, the light emitter(s) 740 and/or detector(s) 745 may be configured to transmit light through a hole or series of holes in the device exterior. This hole or series of holes may be filled in with light-transmissive epoxy (e.g. optical epoxy). The epoxy may form a light pipe that allows light to be transmitted from the light emitter(s) to the skin and from the skin back into the light detector(s). Such technique may provide the advantage that the epoxy may form a watertight seal, preventing water, sweat or other liquid from entering the device body though the hole(s) on the device exterior that allow the light emitter(s) and detector(s) to transmit to, and receive light from, the biometric monitoring device body exterior. An epoxy with a high thermal conductivity may be used to help prevent the light source(s) 745 (e.g., LED's) from overheating.

FIG. 7A illustrates an example embodiment of a photoplethysmography (PPG) light source and photodetector geometry. In the embodiment of FIG. 7A, two light sources 740 are placed on either side of a photodetector 745. These three devices may be located in a protrusion form on the backside of a wristband-type biometric monitoring device (e.g., the side which faces the skin of the user), as described above.

FIGS. 7B and 7C illustrate examples of a physiological metric (e.g., PPG) sensor having a light detector 745 (e.g., photodetector) and two light sources 740 (e.g., LED). Such components may be disposed in a biometric monitoring device that has a protrusion form on the backside. In certain embodiments, light pipes 747 optically connect the LEDs 740 and photodetector 745 with the surface of the user's skin 701. Beneath the skin 701, the light from the light sources 740 may scatter off of blood 703 in the body, some of which may be scattered or reflected back into the photodetector 745.

Figure 8:
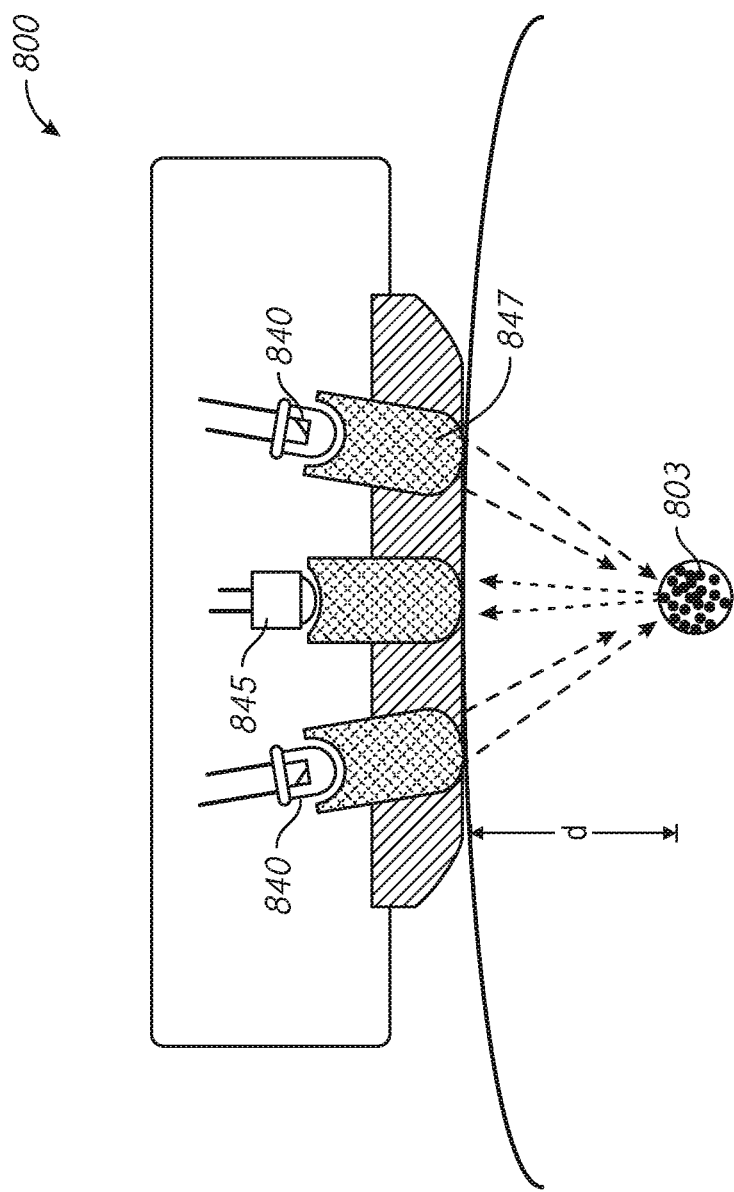
FIG. 8 illustrates an example of an optimized PPG detector according to one or more embodiments.

FIG. 8 illustrates an example of a biometric monitoring device 800 with an optimized PPG detector that has a protrusion with curved sides so as not to discomfort the user. Additionally, the surface of light pipes 847 that optically couple the photodetector 845 and the LEDs 840 to the wearer's skin may be contoured to improve light flux coupling between the LEDs 840 and photodetector(s) 845 and the light pipes 847. The ends of the light pipes that face the user's skin may also be contoured. This contour may focus or defocus light to optimize the PPG signal. For example, the contour may focus emitted light to a certain depth and location that coincides with an area where blood flow is likely to occur. The vertex of these foci may overlap or be very close together so that the photodetector receives the maximum possible amount of scattered light.

In certain embodiments, the biometric monitoring device may include a concave or convex shape, e.g., a lens, on the skin-side of the device, to focus light towards a specific volume at a specific depth in the skin and increase the efficiency of light collected from that point into the photodetector. Where such a biometric monitoring device also employs light pipes to selectively and controllably route light, it may be advantageous to shape the end of the light pipe with a degree of cylindricity, e.g., the end of the light pipe may be a be a cylindrical surface (or portion thereof) defined by a cylinder axis that is nominally parallel to the skin-side (for example, rather than use an axially-symmetric lens). For example, in a wristband-style biometric monitoring device, such a cylindrical lens may be oriented such that the cylinder axis is nominally parallel to the wearer's forearm, which may have the effect of limiting the amount of light that enters such a lens from directions parallel to the person's forearm and increasing the amount of light that enters such a lens from directions perpendicular to the person's forearm—since ambient light is more likely to reach the sensor detection area from directions that are not occluded by the straps of the biometric monitoring device, i.e., along the user's forearm axis, than from directions that are occluded by the straps, i.e., perpendicular to the user's forearm. Such a configuration may improve the signal-to-noise-ratio by increasing the efficiency of light transferred from the emitter onto or into the skin of the user while decreasing "stray" light from being detected or collected by the photodetector. In this way, the signal sampled, measured and/or detected by the photodetector consists less of stray light and more of the user's skin/body response to such emitted light (signal or data that is representative of the response to the emitted light).

In one embodiment, the optical sensors (sources and/or detectors) may be disposed on an interior or skin-side of the biometric monitoring device (i.e., a side of the biometric monitoring device that contacts, touches, and/or faces the skin of the user (hereinafter "skin-side"). (See, for example, FIGS. 2A through 3C). In another embodiment, the optical sensors may be disposed on one or more sides of the device, including the skin-side and one or more sides of the device that face or are exposed to the ambient environment (environmental side). (See, for example, FIGS. 6A through 7).

Figure 9:
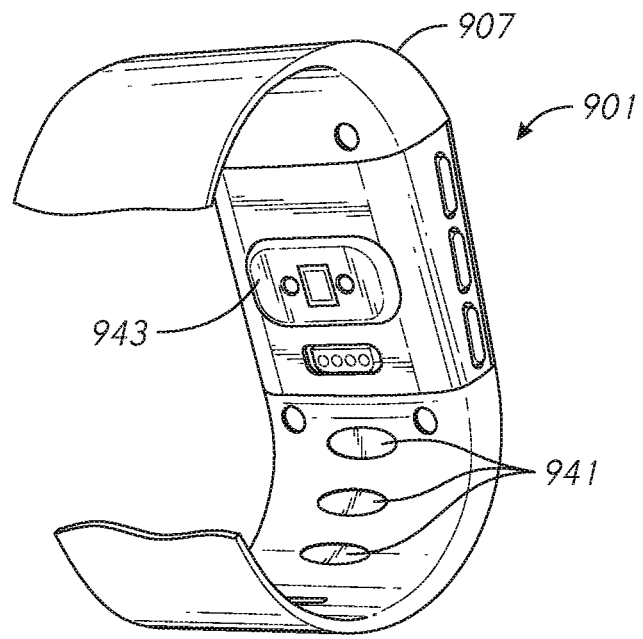
FIG. 9 provides a perspective front and side view of a wearable biometric monitoring device according to one or more embodiments.

FIG. 9 illustrates an example of a portable monitoring device having a band 907 with one or more optical sensors and light emitters 941 disposed in association with the inside of the band. For example, there may be a plurality of photodetectors and photo emitters placed at various sites along the circumference of the interior of the band 907. A heart rate signal-quality metric associated with each site may be calculated to determine the best or set of best sites for estimating the user's heart rate. Subsequently, some of the sites may be disabled or turned off to, for example, reduce power consumption. The device may periodically check the heart rate signal quality at some or all of the sites to enhance, monitor and/or optimize signal and/or power efficiency.

Figure 10:
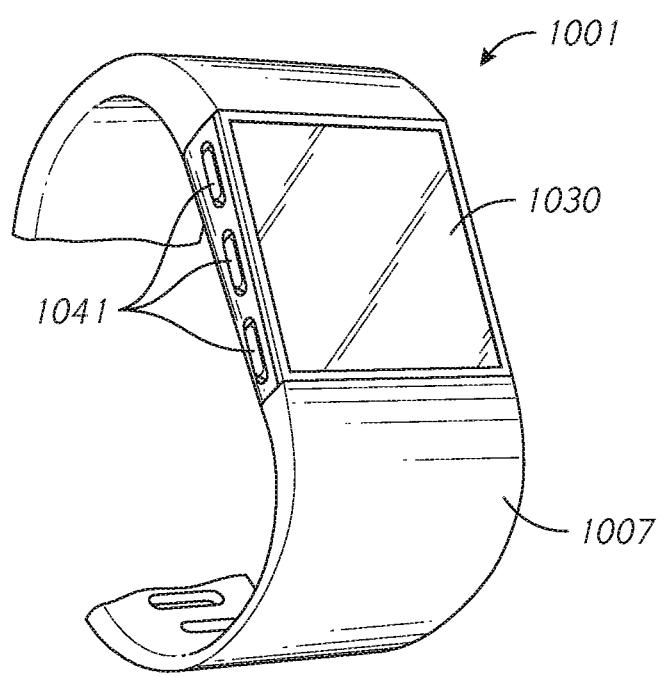
FIG. 10 provides a perspective back and side view of a wearable biometric monitoring device according to one or more embodiments.

FIG. 10 illustrates an example of a portable biometric monitoring device 1001 having a display 1030 and wristband 1007. Additionally, optical PPG (e.g., heart rate) detection sensors and/or emitters 1041 may be located on the side of the biometric monitoring device. In one embodiment, these may be located in side-mounted buttons.

All of the optical sensors discussed herein may be used in conjunction with other sensors to improve detection of the data described above or be used to augment detection of other types of physiological or environmental data.

Figure 11A:
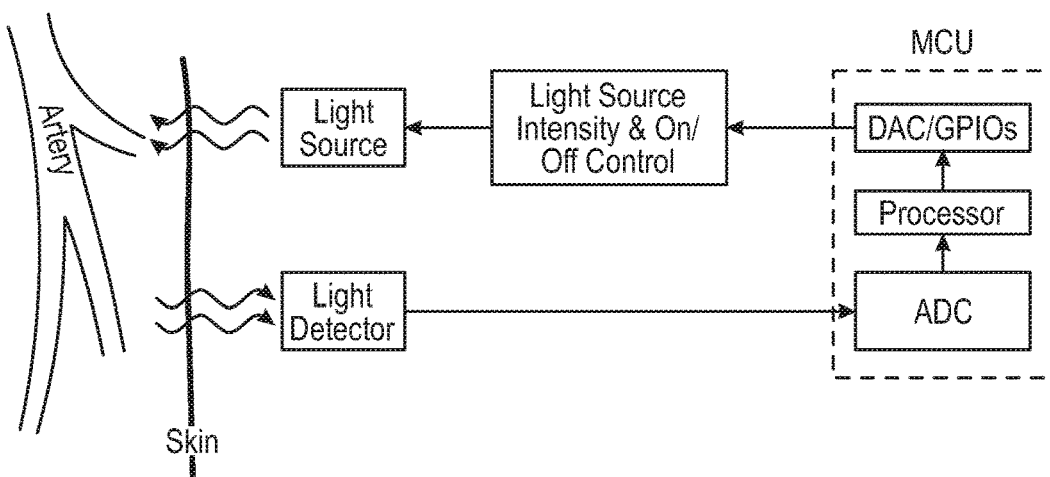
FIG. 11A illustrates an example block diagram of a PPG sensor which has a light source, light detector, ADC, processor, DAC/GPIOs, and light source intensity and on/off control according to one or more embodiments.

FIG. 11A depicts an example schematic block diagram of an optical heart rate sensor where light is emitted from a light source toward the user's skin and the reflection of such light from the skin/internal body of the user is sensed by a light detector, the signal from which is subsequently digitized by an analog to digital converter (ADC). The intensity of the light source may be modified (e.g., through a light source intensity control module) to maintain a desirable reflected signal intensity. For example, the light source intensity may be reduced to avoid saturation of the output signal from the light detector. As another example, the light source intensity may be increased to maintain the output signal from the light detector within a desired range of output values. Notably, active control of the system may be achieved through linear or nonlinear control methods such as proportional-integral-derivative (PID) control, fixed step control, predictive control, neural networks, hysteresis, and the like, and may also employ information derived from other sensors in the device such as motion, galvanic skin response, etc. FIG. 11A is provided for illustration and does not limit the implementation of such a system to, for instance, an ADC integrated within a MCU, or the use of a MCU for that matter. Other possible implementations include the use of one or more internal or external ADCs, FPGAs, ASICs, etc.

Figure 11B:
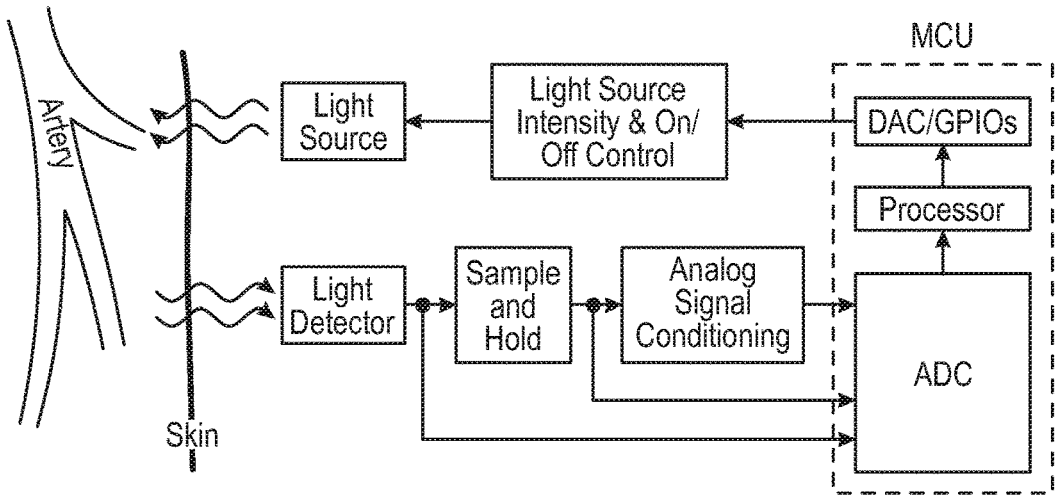
FIG. 11B illustrates an example block diagram of a PPG sensor that is similar to that of FIG. 11A which additionally uses a sample-and-hold circuit as well as analog signal conditioning according to one or more embodiments.

In another embodiment, system with an optical heart rate sensor may incorporate the use of a sample-and-hold circuit (or equivalent) to maintain the output of the light detector while the light source is turned off or attenuated to save power. In embodiments where relative changes in the light detector output are of primary importance (e.g., heart rate measurement), the sample-and-hold circuit may not have to maintain an accurate copy of the output of the light detector. In such cases, the sample-and-hold may be reduced to, for example, a diode (e.g., Schottky diode) and capacitor. The output of the sample-and-hold circuit may be presented to an analog signal conditioning circuit (e.g., a Sallen-Key band-pass filter, level shifter, and/or gain circuit) to condition and amplify the signal within frequency bands of interest (e.g., 0.1 Hz to 10 Hz for cardiac or respiratory function), which may then be digitized by the ADC. See, for example, FIG. 11B.

Figure 11C:
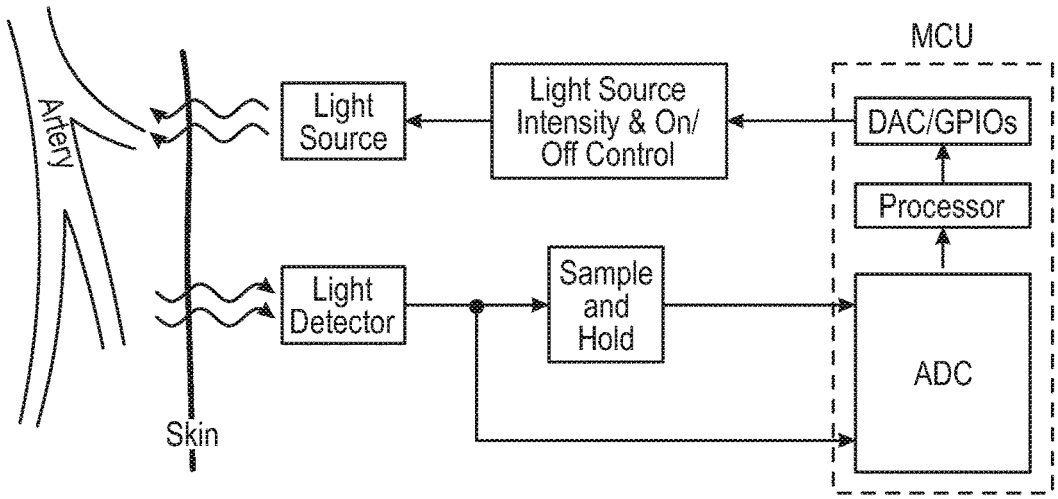
FIG. 11C illustrates an example block diagram of a PPG sensor that is similar to that of FIG. 11A which additionally uses a sample-and-hold circuit according to one or more embodiments.
Figure 11D:
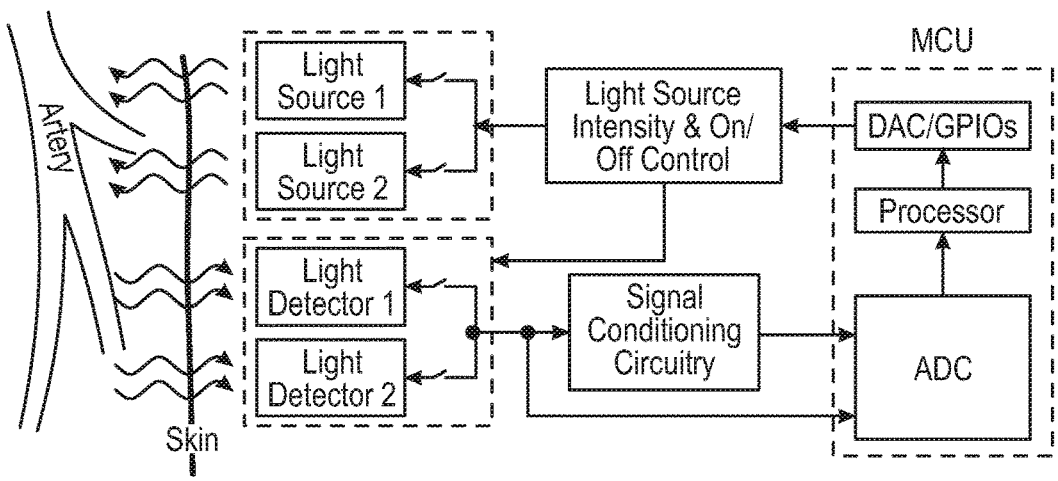
FIG. 11D illustrates an example block diagram of a PPG sensor having multiple switchable light sources and detectors, light source intensity/on and off control, and signal conditioning circuitry according to one or more embodiments.

In operation, circuit topologies such as those already described herein (e.g. a sample-and-hold circuit) remove the DC and low frequency components of the signal and help resolve the AC component related to heart rate and/or respiration. The embodiment may also include the analog signal conditioning circuitry for variable gain settings that can be controlled to provide a suitable signal (e.g., not saturated). The performance characteristics (e.g., slew rate and/or gain bandwidth product) and power consumption of the light source, light detector, and/or sample-and-hold may be significantly higher than the analog signal conditioning circuit to enable fast duty cycling of the light source. In some embodiments, the power provided to the light source and light detector may be controlled separately from the power provided to the analog signal conditioning circuit to provide additional power savings. Alternatively, or additionally, the circuitry can use functionality such as an enable, disable and/or shutdown to achieve power savings. In another embodiment, the output of the light detector and/or sample-and-hold circuit may be sampled by an ADC in addition to or in lieu of the analog signal conditioning circuit to control the light intensity of the light source or to measure the physiologic parameters of interest when, for example, the analog signal conditioning circuit is not yet stable after a change to the light intensity setting. Notably, because the physiologic signal of interest is typically small relative to the inherent resolution of the ADC, in some embodiments, the reference voltages and/or gain of the ADC may be adjusted to enhance signal quality and/or the ADC may be oversampled. In yet another embodiment, the device may digitize the output of only the sample-and-hold circuit by, for example, oversampling, adjusting the reference voltages and/or gain of the ADC, or using a high resolution ADC. See, for example, FIG. 11C.

in some embodiments, the color or wavelength of the light emitted by the light source, e.g., an LED (or set of LEDs), may be modified, adjusted, and/or controlled in accordance with a predetermined type of physiological data being acquired or conditions of operation. Here, the wavelength of the light emitted by the light source may be adjusted and/or controlled to optimize and/or enhance the "quality" of the physiological data obtained and/or sampled by the detector. For example, the color of the light emitted by the LED may be switched from infrared to green when the user's skin temperature or the ambient temperature is cool in order to enhance the signal corresponding to cardiac activity. (See, for example, FIG. 11D)

Ambient Light Determination

Figure 11E:
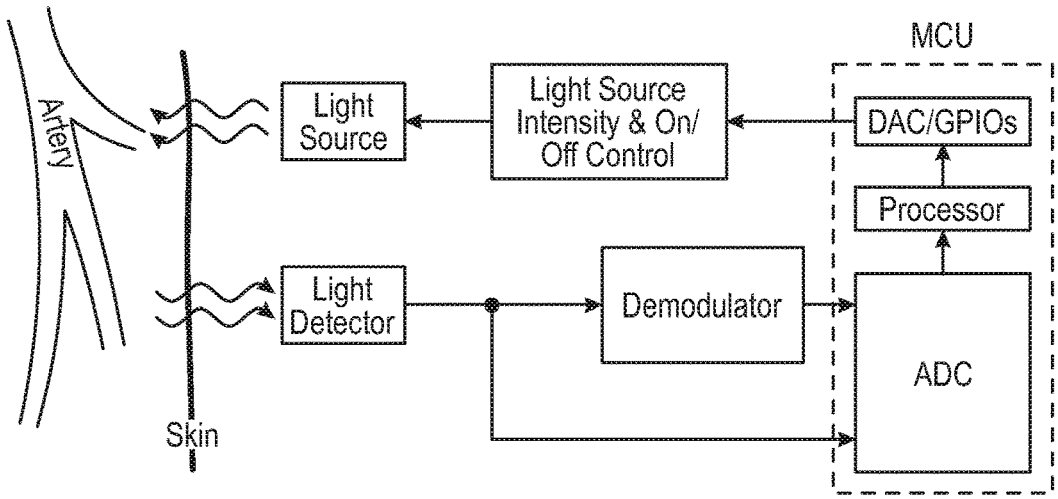
FIG. 11E illustrates an example block diagram of a PPG sensor which uses synchronous detection. To perform this type of PPG detection, it has a demodulator according to one or more embodiments.
Figure 11F:
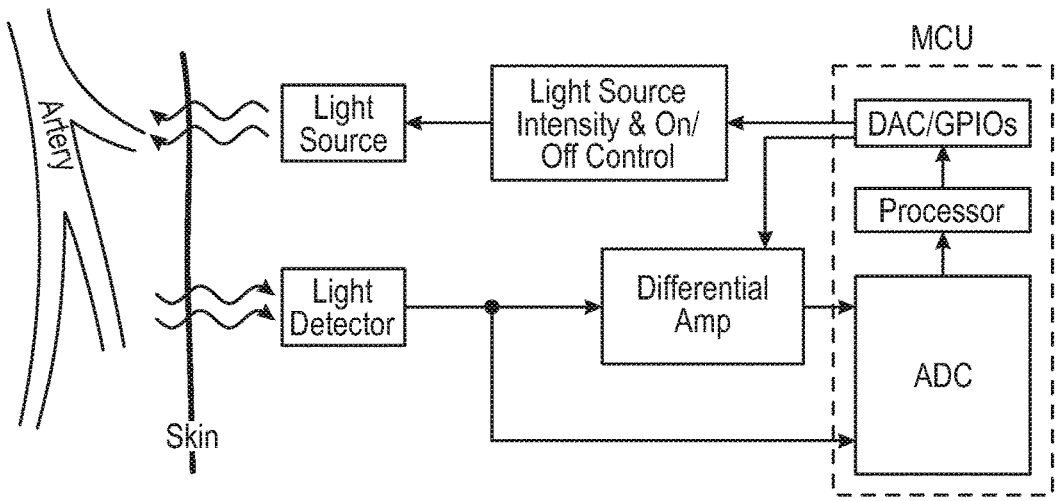
FIG. 11F illustrates an example block diagram of a PPG sensor which, in addition to the features of the sensor illustrated in FIG. 11A, has a differential amplifier according to one or more embodiments.

In another embodiment, the sensor device may incorporate a differential amplifier to amplify the relative changes in the output of the light detector. See, for example, FIG. 11F. In some embodiments, a digital average or digital low-pass filtered signal may be subtracted from the output of the light detector. This modified signal may then be amplified before it is digitized by the ADC. In another embodiment, an analog average or analog low-pass filtered signal may be subtracted from the output of the light detector through, for example, the use of a sample-and-hold circuit and analog signal conditioning circuitry. The power provided to the light source, light detector, and differential amplifier may be controlled separately from the power provided to the analog signal conditioning circuit to improve power savings.

In another embodiment, a signal (voltage or current, depending on the specific sensor implementation) may be subtracted from the raw PPG signal to remove any bias in the raw PPG signal and therefore increase the gain or amplification of the PPG signal that contains heart rate (or other circulatory parameters such as heart rate variability) information. This signal may be set to a default value in the factory, to a value based on the user's specific skin reflectivity, absorption, and/or color, and/or may change depending on feedback from an ambient light sensor, or depending on analytics of the PPG signal itself. For example, if the PPG signal is determined to have a large DC offset, a constant voltage may be subtracted from the PPG signal to remove the DC offset and enable a larger gain, therefore improving the PPG signal quality. The DC offset in this example may result from ambient light (for example from the sun or from indoor lighting) reaching the photodetector from or reflected light from the PPG light source.

In another embodiment, a differential amplifier may be used to measure the difference between current and previous samples rather than the magnitude of each signal. Since the magnitude of each sample is typically much greater than the difference between each sample, a larger gain can be applied to each measurement, therefore improving the PPG signal quality. The signal may then be integrated to obtain the original time domain signal.

In another embodiment, the light detector module may incorporate a transimpedance amplifier stage with variable gain. Such a configuration may avoid or minimize saturation from bright ambient light and/or bright emitted light from the light source. For example, the gain of the transimpedance amplifier may be automatically reduced with a variable resistor and/or multiplexed set of resistors in the negative feedback path of the transimpedance amplifier. In some embodiments, the device may incorporate little to no optical shielding from ambient light by amplitude-modulating the intensity of the light source and then demodulating the output of the light detector (e.g., synchronous detection). See, for instance, FIG. 11E. In other aspects, if the ambient light is of sufficient brightness to obtain a heart rate signal, the light source may be reduced in brightness and/or turned off completely.

Figure 11G:
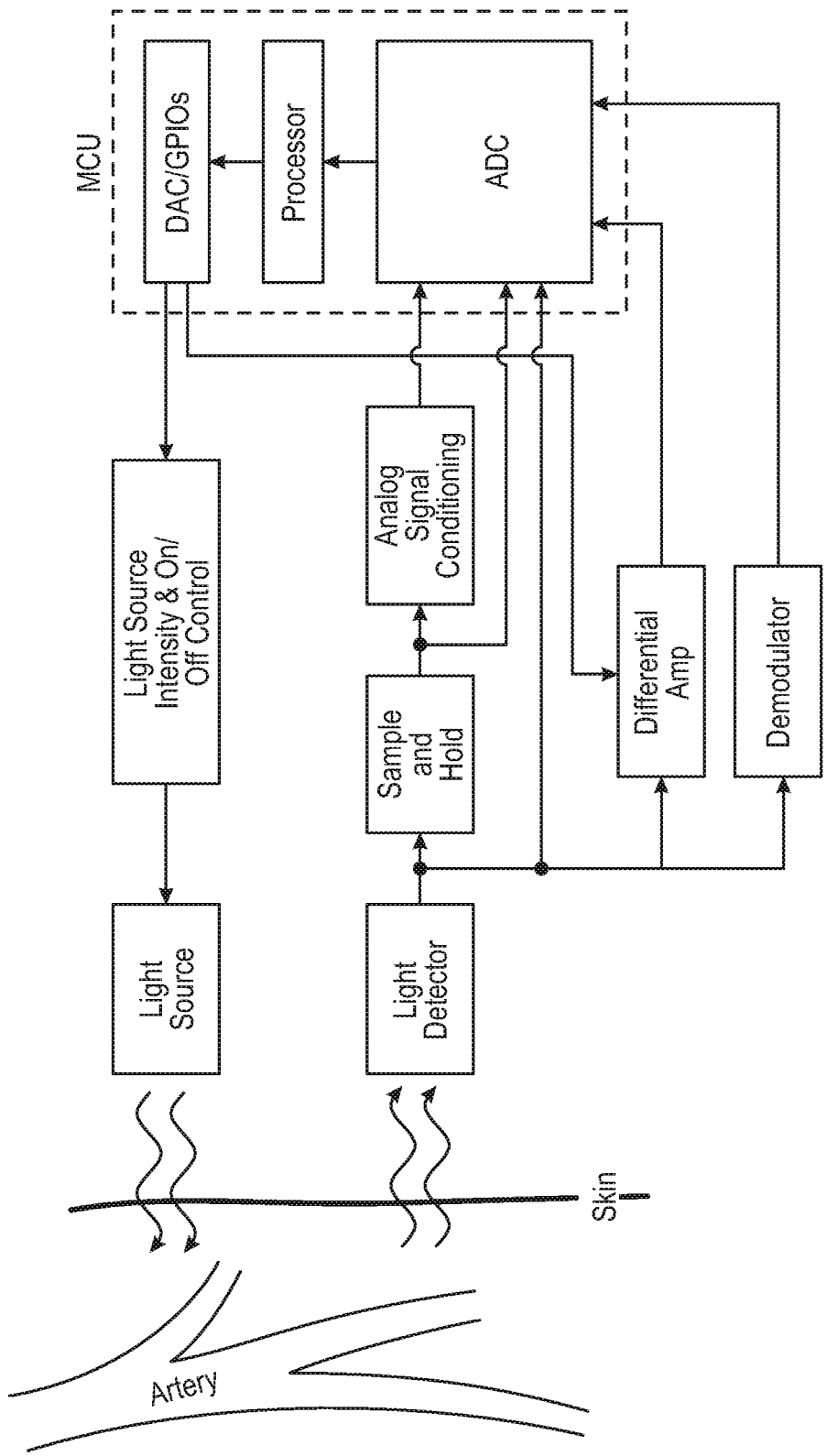
FIG. 11G illustrates an example block diagram of a PPG sensor according to one or more embodiments.

In yet another embodiment, the aforementioned processing techniques may be used in combination to optically measure physiological parameters of the user. See, for example, FIG. 11G. This topology may allow the system to operate in a low power measurement state and circuit topology when applicable and adapt to a higher power measurement state and circuit topology as necessary. For instance, the system may measure the physiologic parameter (e.g., heart rate) of interest using analog signal-conditioning circuitry while the user is immobile or sedentary to reduce power consumption, but switch to oversampled sampling of the light detector output directly while the user is active.

Circuits for Performing PPG

PPG circuitry may be optimized to obtain the best quality signal regardless of a variety of environmental conditions including, but not limited to, motion, ambient light, and skin color. The following circuits and techniques may be used to perform such optimization (see FIGS. 12A through 12J); a sample-and-hold circuit and differential/instrumentation amplifier which may be used in PPG sensing. The output signal is an amplified difference between current and previous sample, referenced to a given voltage. controlled current source to offset "bias" current prior to transimpedance amplifier. This allows greater gain to be applied at transimpedance amplifier stage. a sample-and-hold circuit for current feedback applied to photodiode (prior to transimpedance amplifier). This can be used for ambient light removal, or "bias" current removal, or as a pseudo differential amplifier (may require dual rails). a differential/instrumentation amplifier with ambient light cancellation. a photodiode offset current generated dynamically by a DAC. a photodiode offset current generated dynamically by controlled voltage source. ambient light removal using a "switched capacitor" method. photodiode offset current generated by a constant current source (also can be done with a constant voltage source and a resistor). ambient light removal and differencing between consecutive samples. ambient light removal and differencing between consecutive samples.

Figure 12A:
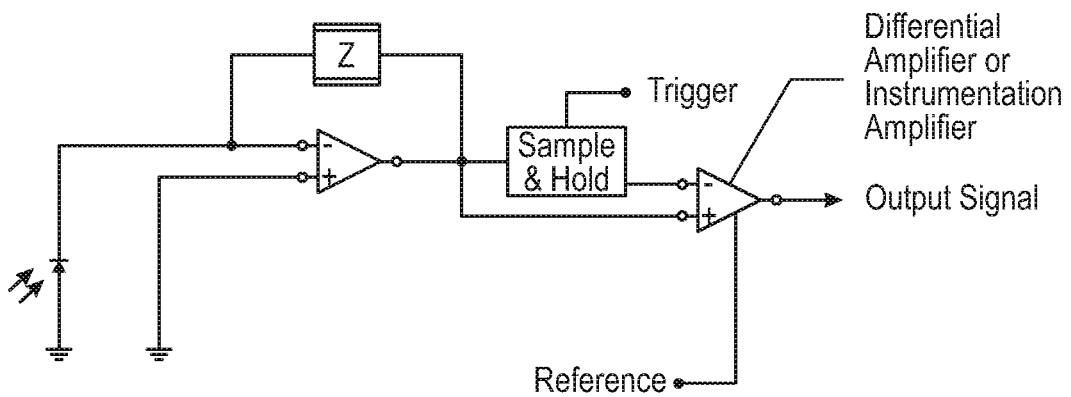
FIG. 12A illustrates an example schematic of a sample-and-hold circuit and differential/instrumentation amplifier which may be used in PPG sensing according to one or more embodiments.

FIG. 12A illustrates an example schematic of a sample-and-hold circuit and differential/instrumentation amplifier which may be used in PPG sensing. The output signal in such a circuit may be an amplified difference between a current sample and a previous sample, referenced to a given voltage.

Figure 12B:
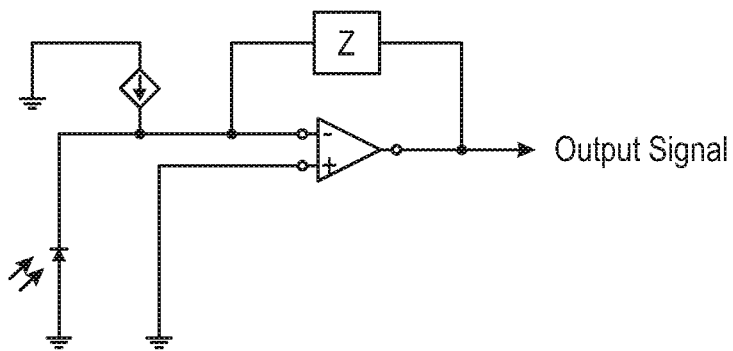
FIG. 12B illustrates an example schematic of a circuit for a PPG sensor using a controlled current source to offset "bias" current prior to a transimpedance amplifier according to one or more embodiments.

FIG. 12B illustrates an example schematic of a circuit for a PPG sensor using a controlled current source to offset "bias" current prior to a transimpedance amplifier. This allows greater gain to be applied at the transimpedance amplifier stage.

Figure 12C:
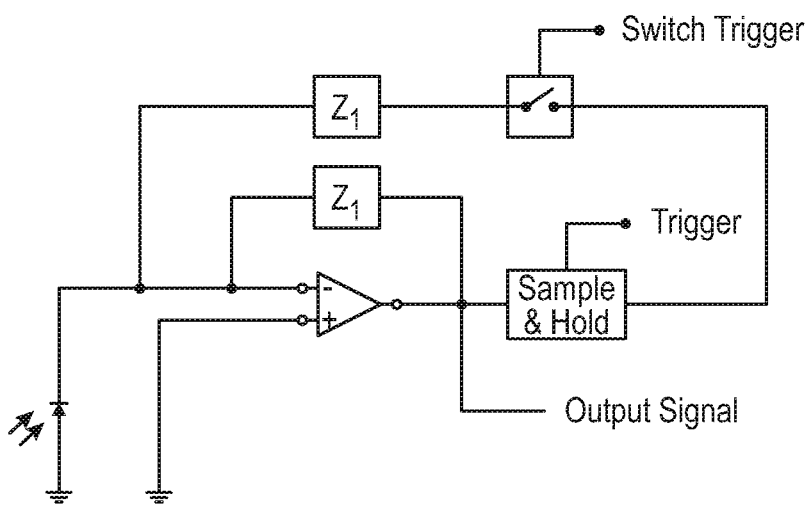
FIG. 12C illustrates an example schematic of a circuit for a PPG sensor using a sample-and-hold circuit for current feedback applied to photodiode according to one or more embodiments.

FIG. 12C illustrates an example schematic of a circuit for a PPG sensor using a sample-and-hold circuit for current feedback applied to photodiode (prior to a transimpedance amplifier). This circuit may be used for ambient light removal, or "bias" current removal, or as a pseudo-differential amplifier.

Figure 12D:
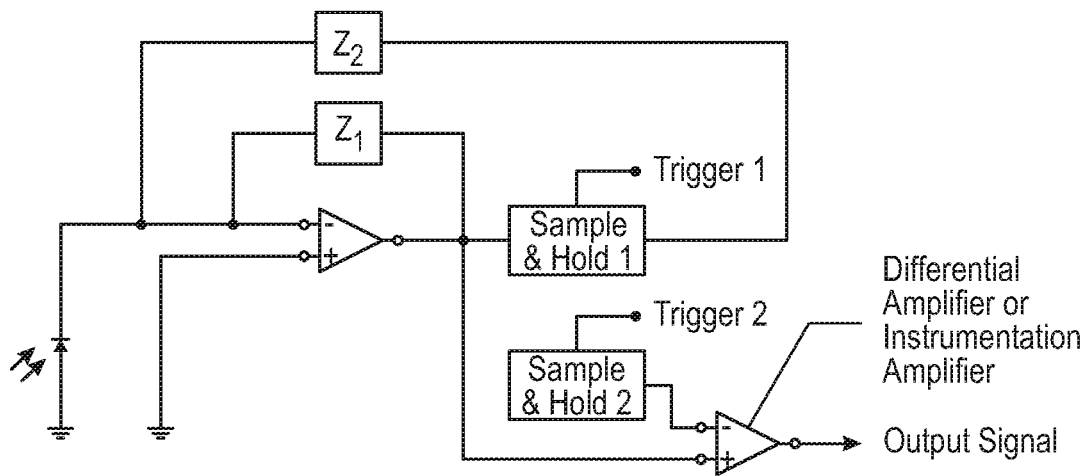
FIG. 12D illustrates an example schematic of a circuit fora PPG sensor using a differential/instrumentation amplifier with ambient light cancellation functionality according to one or more embodiments.

FIG. 12D illustrates an example schematic of a circuit for a PPG sensor using a differential/instrumentation amplifier with ambient light cancellation functionality.

Figure 12E:
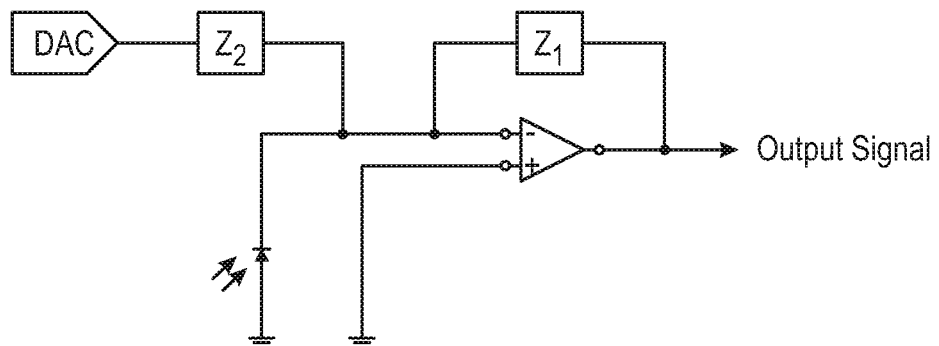
FIG. 12E illustrates an example schematic of a circuit for a PPG sensor using a photodiode offset current generated dynamically by a DAC according to one or more embodiments.

FIG. 12E illustrates an example schematic of a circuit for a PPG sensor using a photodiode offset current generated dynamically by a DAC.

Figure 12F:
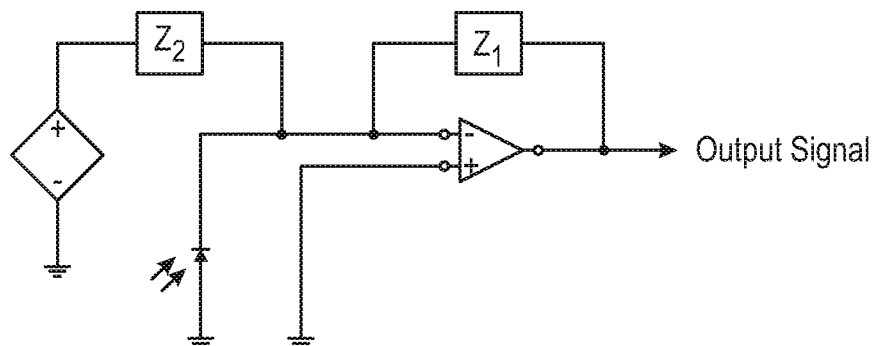
FIG. 12F illustrates an example schematic of a circuit for a PPG sensor using a photodiode offset current generated dynamically by a controlled voltage source according to one or more embodiments.

FIG. 12F illustrates an example schematic of a circuit for a PPG sensor using a photodiode offset current generated dynamically by a controlled voltage source.

Figure 12G:
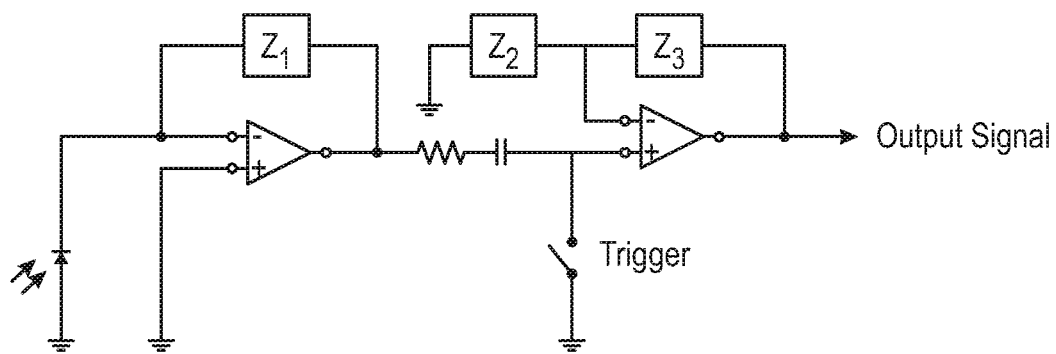
FIG. 12G illustrates an example schematic of a circuit for a PPG sensor including ambient light removal functionality using a "switched capacitor" method according to one or more embodiments.

FIG. 12G illustrates an example schematic of a circuit for a PPG sensor including ambient light removal functionality using a "switched capacitor" method.

Figure 12H:
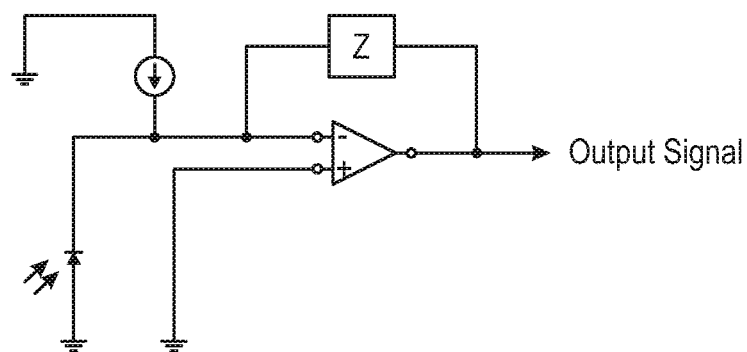
FIG. 12H illustrates an example schematic of a circuit fora PPG sensor that uses a photodiode offset current generated by a constant current source according to one or more embodiments.

FIG. 12H illustrates an example schematic of a circuit for a PPG sensor that uses a photodiode offset current generated by a constant current source (this may also be done using a constant voltage source and a resistor).

Figure 12I:
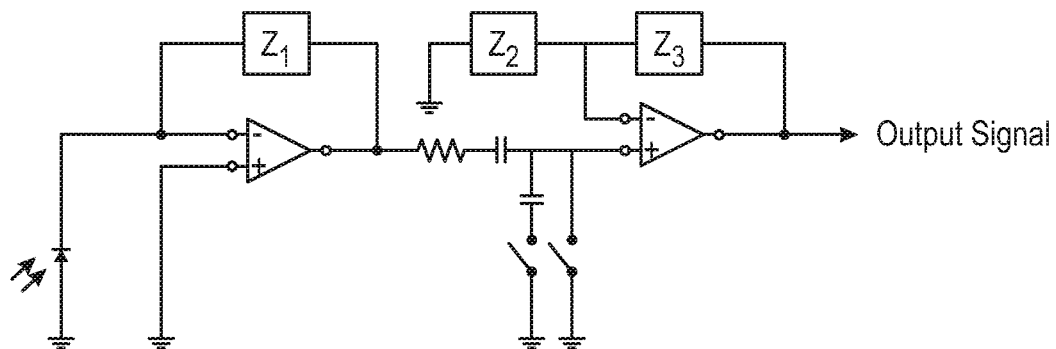
FIG. 12I illustrates an example schematic of a circuit for a PPG sensor that includes ambient light removal functionality and differencing between consecutive samples according to one or more embodiments.

FIG. 12I illustrates an example schematic of a circuit for a PPG sensor that includes ambient light removal functionality and differencing between consecutive samples.

Figure 12J:
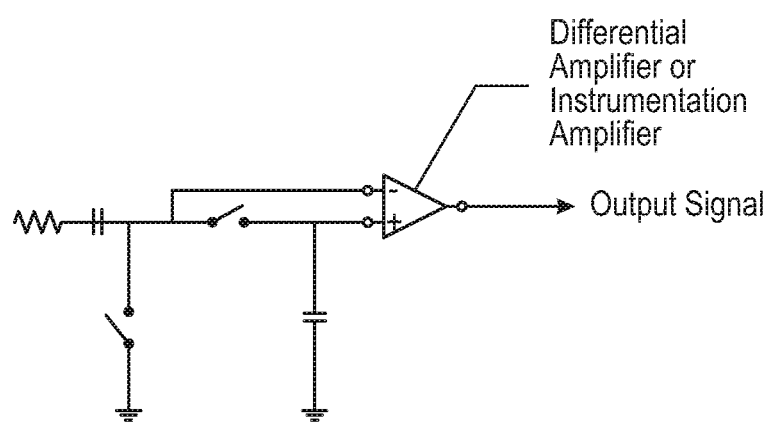
FIG. 12J illustrates an example schematic of a circuit for ambient light removal and differencing between consecutive samples according to one or more embodiments.

FIG. 12J illustrates an example schematic of a circuit for ambient light removal and differencing between consecutive samples.

Various circuits and concepts related to heart rate measurement using a PPG sensor are discussed in more detail in U.S. Provisional Patent Application No. 61/946,439, filed Feb. 28, 2014 which is hereby incorporated by reference with respect to content directed at heart rate measurements with a PPG sensor and at circuits, methods, and systems for performing such measurements.

Figure 13:
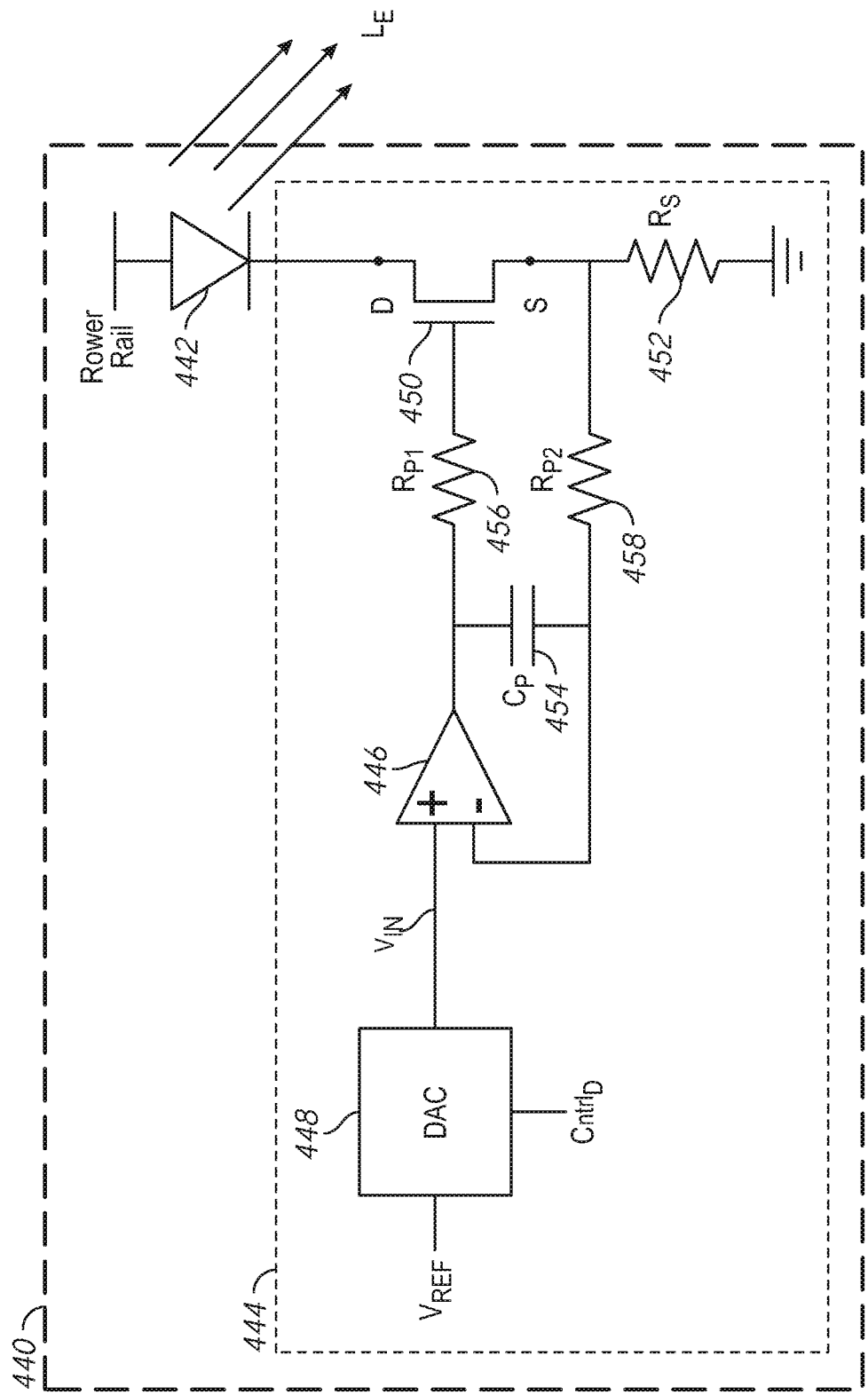
FIG. 13 shows an example light emission driver circuit for driving a light emitter to emit a light signal onto a region of the skin of a user according to one or more embodiments.
Figure 14:
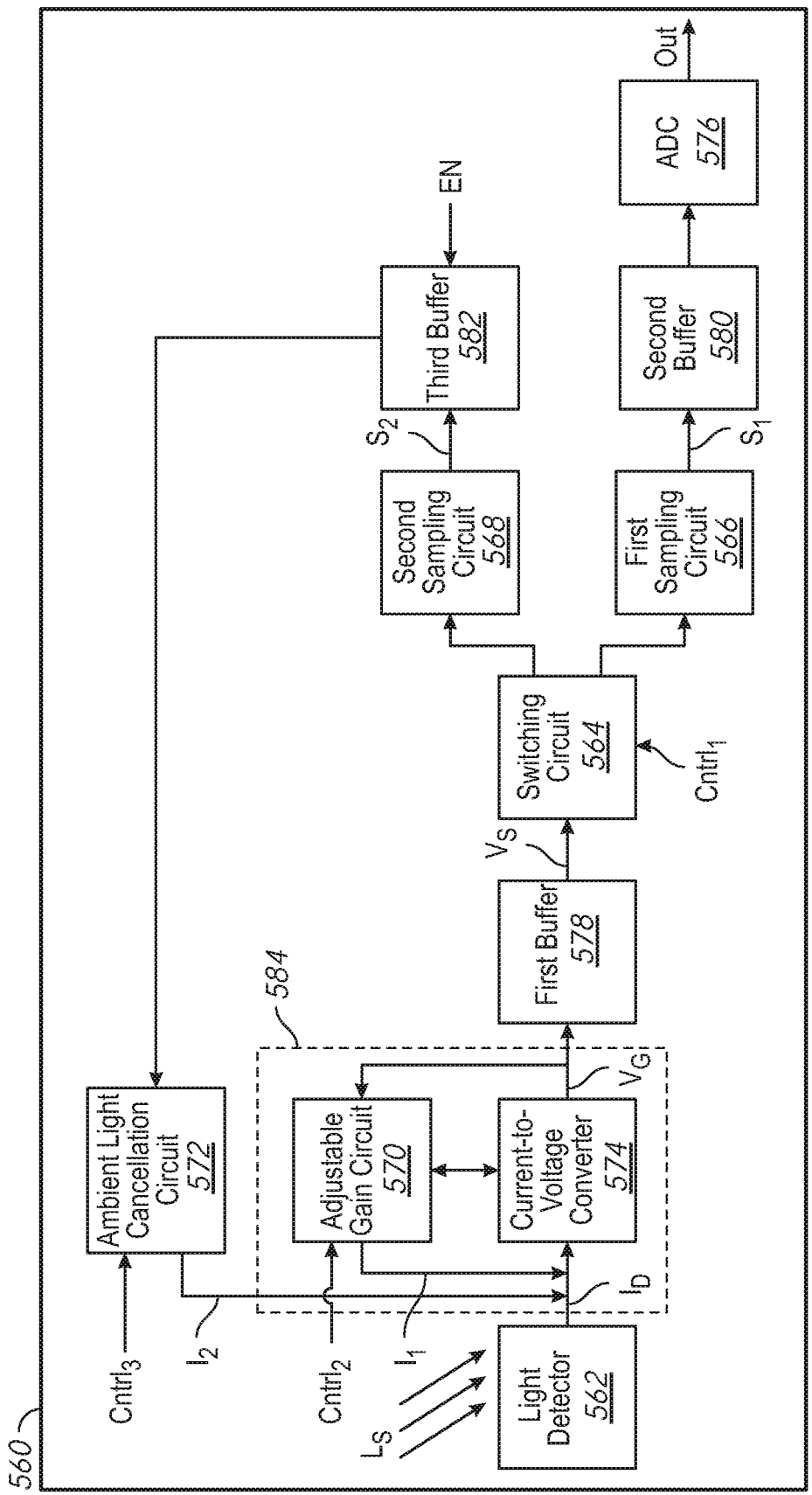
FIG. 14 shows a block diagram of an example light detection circuit for detecting a scattered light signal and for outputting an output signal based on the scattered light signal according to one or more embodiments.
Figure 15:
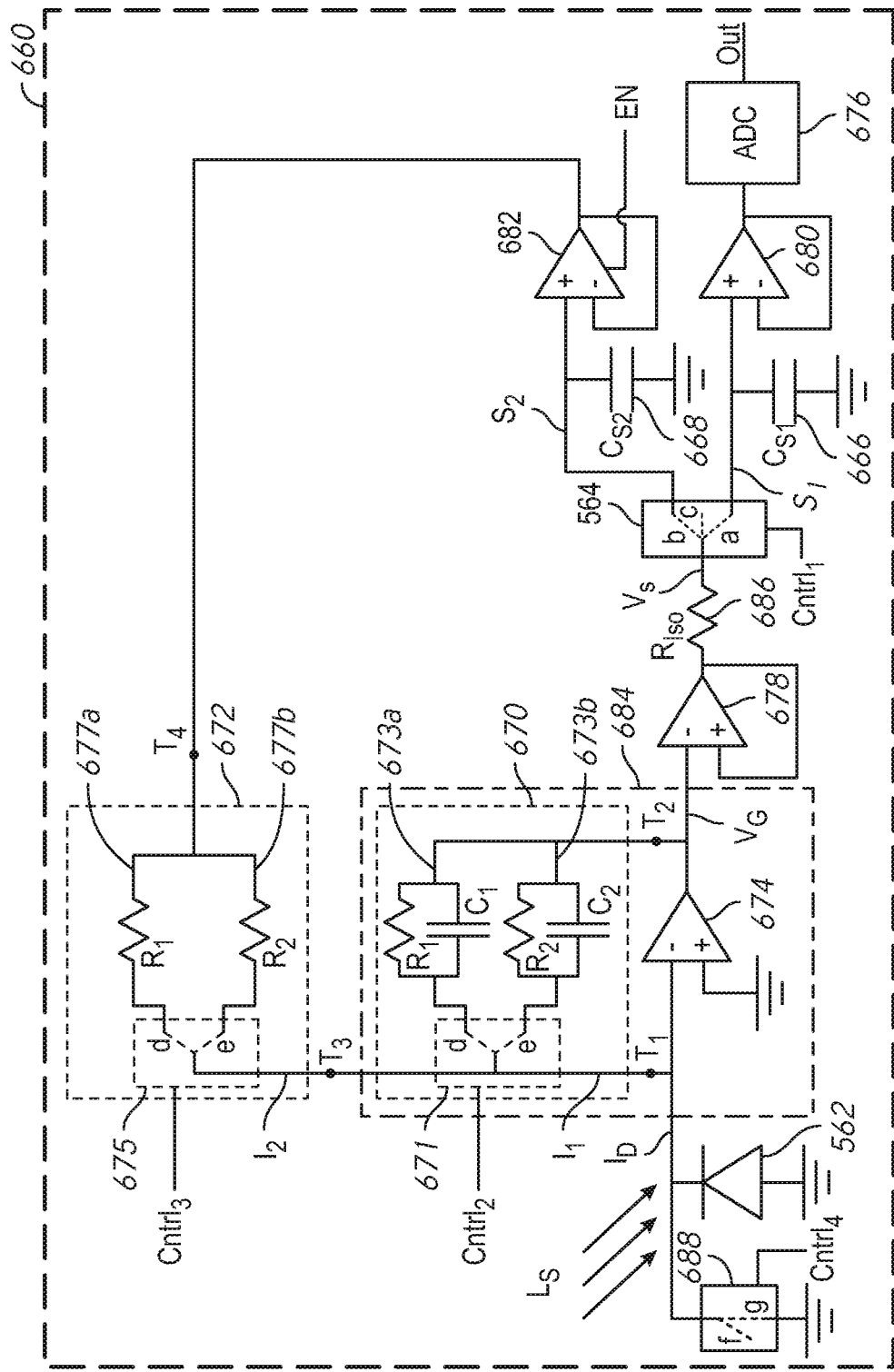
FIG. 15 shows an example circuit for implementing the light detection circuit of FIG. 14 according to one or more embodiments.

FIG. 13 shows an example light emission driver circuit 440 for driving a light emitter to emit an incident light signal $L_E$ onto a region of the skin of a user according to some implementations. For example, the light emission driver circuit 440 can be used in conjunction with the any light source of a biometric monitoring device of the present disclosure. As described above, a portion of the incident light signal $L_E$ is reflected, refracted, or otherwise scattered by the skin of the user, and more particularly, the arteries below the skin of the user. The portion of the incident light scattered by the skin of the user also is referred to herein as the "scattered light signal" $L_S$. FIG. 14 shows a block diagram of an example light detection circuit 560 for detecting the scattered light signal $L_S$ and for outputting an output signal OUT based on the scattered light signal $L_S$ according to some implementations. For example, the light detection circuit 560 can be used in conjunction with any of the light detectors of physiological metric sensor modules of the present disclosure. FIG. 15 shows an example circuit 660 for implementing the light detection circuit 560 of FIG. 14 according to some implementations.

The light emission driver circuit 440 includes, at a high level, a voltage-controlled current source that drives a light emitter 442 arranged to emit an incident light signal $L_E$ onto a region of the skin of a user. For example, the light emitter 442 can be the light emitter 336 described above and, as described above, can include one or more LEDs, laser, or other light sources. In the illustrated implementation, the voltage-controlled current source is implemented by a driver circuit 444 that powers the light emitter 442 based on one or more control signals $Cntrl_D$ received from, for example, the processing unit 104. In some implementations, the driver circuit 44 is configured to drive (or "power") the light emitter 442 for certain intervals of time based on the control signals $Cntrl_D$ (for example, when enabled by a control signal) such that the light emitter 442 emits a light signal $L_E$ in the form of a series (or "train") of pulses during the intervals of time. For example, in some cases, the light emitter 442 may be a relatively costly component of the portable monitoring device 100 in terms of power consumption. Thus, it may be desirable to power the light emitter 442 for only a short amount of time, hence the use of a series of short pulses.

While other implementations of a driver circuit 444, including other implementations of a voltage-controlled current source, are within the scope of this disclosure, in the illustrated implementation the driver circuit 444 includes an operational amplifier 446 having a first input terminal, a second input terminal and an output terminal. The driver circuit also includes a digital to analog converter (DAC) 448 electrically coupled with the first input terminal of the operational amplifier 446. The DAC 448 provides an input signal $V_{IN}$ to the first input terminal of the operational amplifier 446 based on a reference signal $V_{REF}$ and the control signals $Cntrl_D$. A power supply rail supplies a power source to a first terminal of the light emitter 442.

The driver circuit 440 may also include a switch, and more particularly, a transistor 450. In the illustrated implementation, the transistor 450 may be a metal-oxide-semiconductor field-effect transistors (MOSFET), such as an n-channel MOSFET (an "NMOS transistor"). In some other implementations, the transistor 450 may be implemented by another type of switch or transistor such as, for example, a bipolar junction transistor. The transistor 450 includes a gate terminal, a drain terminal D and a source terminal S. In certain embodiments, the gate terminal may be electrically coupled with the output terminal of the operational amplifier 446. The drain terminal D may be electrically coupled with a second terminal of the light emitter 442. The source terminal S may be electrically coupled, via a resistor 452 having a resistance $R_S$, to a reference voltage, such as a ground. The source terminal S may be further electrically coupled with the second input terminal of the operational amplifier 446 for providing a feedback signal to the operational amplifier. In the illustrated implementation, the driver circuit 444 further includes a capacitor 454 having a capacitance $C_P$ electrically coupled between the output terminal of the operational amplifier 446 and the second input terminal of the operational amplifier. The driver circuit 444 also can include a resistor 456 having a resistance $R_{P1}$; between the output terminal of the operational amplifier 446 and the gate terminal of the transistor 450. The driver circuit 444 also can include a resistor 458 having a resistance $R_{P2}$; between the source terminal S of the transistor 450 and the second input terminal of the operational amplifier 446. The resistances $R_{P1}$; and $R_{P2}$; and the capacitance $C_P$ can be configured to tune the driver circuit 444 to obtain fast settling times, which can save power because can be operated for less time, while maintaining stability. During operation, the operational amplifier 446 may be configured to, based on the feedback signal received at the second input terminal of the operational amplifier, maintain a substantially constant voltage across the resistor 452. In this way, the driver circuit 444 behaves as a constant current source with a current $I_E=V_{IN}/R_S$ passing through the light emitter 442 and resistor 452. This may be desirable because any change or ripple in the current $I_E$ provided to the light emitter 452 will result in undesired artifacts in the incident light signal $L_E$, which will also show in the scattered light signal $L_S$.

Referring now to FIG. 14, the light detection circuit 560 may be configured to detect a scattered light signal $L_S$, (for example, a portion of the incident light signal $L_E$ scattered by the skin of the user), generate a detected electrical signal $I_D$ based on the scattered light signal, sample the electrical signal to generate a sampled signal $S_1$, and digitize the sampled signal to generate an output signal OUT that represents, for example, heart rate data. As described above, ambient light conditions, skin color (pigmentation) and user motion all can make it difficult to extract a user's heart rate from data signal. In some implementations, the light detection circuit 560 may be configured to correct for a low frequency or "DC" offset resulting from ambient light. For example, ambient light conditions can change as a user moves or changes orientation (for example, hand or body) or as external lighting conditions (for example, sun light or interior lighting) change over time. In some implementations, the light detection circuit 560 may be configured to correct for ambient light conditions by effectively subtracting an ambient light component of the detected signal $I_D$ obtained when a light source (for example, the light emitter 334) may be off from the detected signal when the light source may be on and the signal may be to be sampled.

In some implementations, the light detection circuit 560 also may be configured to adjust a gain of the detected signal $I_D$ to prevent saturation of various electrical components (for example, operational amplifiers) of the light detection circuit 560 or to bring the values of the sampled signal $S_1$ into a range that may be suitable for an ADC that digitizes the sampled signal to generate the output signal OUT. For example, because the time-varying "AC" component of the scattered light signal $L_S$ due to the user's cardiac output can be relatively small in comparison to the low frequency or "DC" component due to ambient light, and because it may be desirable to use high frequency short pulses to reduce the power consumption of the light emitter 442, it may be desirable to subtract the DC ambient light component prior to the sampled signal reaching the ADC. More specifically, if the DC ambient component is not subtracted, the ADC may not be able to take measurements/receive data at the speed for which it may be desired to pulse the emitted light because the detected signal may be so large that the ADC can't resolve the desired AC component at the desired bit depth in the short time required (for example, high precision/high bit depth ADCs tend to be slow because of the processing requirements). Additionally, it can be advantageous to for the light detection circuit 560 to adjust the gain of the detected light signal $I_D$ to account for differences in users' skin tones (pigmentations). For example, different skin tones will absorb and scatter light differently. For example, because darker skin tones can absorb more light and scatter less light, it can be desirable to increase the gain of the detected light signal $I_D$.

The light detection circuit 560 includes a light detector 562 positioned and configured to receive (or "sense" or "detect") at least a portion of the scattered light signal $L_S$ and to generate the detected electrical signal $I_D$ based on the received light. In some implementations, the light detector 562 may be configured to generate the first electrical signal $I_D$ in the form of a time-varying current signal. In such implementations, the magnitude of the current in the first electrical signal $I_D$ may be proportional to the intensity of the scattered light signal $L_S$ (and ambient light) currently being received by the light detector 562 in its detectable range of wavelengths. In some other implementations, the light detector 562 can be configured to generate the first electrical signal $I_D$ in the form of a time-varying voltage signal. In such implementations, the magnitude of the voltage in the first electrical signal $I_D$ would be proportional to the intensity of the scattered light signal $L_S$ (and ambient light) currently being received by the light detector in its detectable range of wavelengths.

In accordance with certain embodiments, where the generated electrical signal $I_D$, or other signal derived at least in part therefrom, is representative of detected light while the light emitter 442 (see FIG. 13) is off, such signal may be analyzed or otherwise utilized to make an ambient lighting condition determination upon which display brightness level setting modification for an associated electronic display is based.

The light detection circuit 560 may also include a switching circuit 564. The switching circuit 564 can be implemented using a variety of suitable switching technologies including one or more analog or digital switching elements. For example, in some implementations, the switching circuit 564 includes an analog integrated circuit. In some implementations, the first switching circuit 564 may be comprised of one or more transistors, such as, for example, one or more pairs of MOSFETs (for example, where each pair includes an NMOS device and a P-channel MOSFET (PMOS) device). In various implementations, the switching circuit 564 includes at least a first configuration a and a second configuration b (in some implementations, the switching circuit 564 also includes a third configuration c). The switching circuit 564 may be configured to receive a voltage signal $V_S$ that may be based on the detected signal $I_D$, as described in more detail below. The switching circuit 564 also may be configured to receive one or more first control signals $Cntrl_1$ received from, for example, the processing unit 104. The switching circuit 564 switches among at least the first configuration a and the second configuration b based on the one or more first control signals $Cntrl_1$.

The light detection circuit 560 also includes a first sampling circuit 566 configured to sample a value of the voltage signal $V_S$ when the switching circuit 564 may be in the first configuration a. The light detection circuit 560 also includes a second sampling circuit 568 configured to sample a value of the voltage signal $V_S$ when the first switching circuit 564 may be in the second configuration b.

The light detection circuit 560 may also include an adjustable gain circuit 570 configured to provide (or "output" or "set") a signal $I_1$ (for example, a current signal) to adjust a gain of the voltage signal $V_S$ relative to the detected signal $I_D$ when the first switching circuit 564 may be in the first configuration. As described above, it can be desirable to adjust the gain so that the light detection circuit 560 can accurately and reliably detect the scattered light signal $L_S$ so that, for example, an analog-to-digital converter (ADC) 576 can resolve a digital signal from the sampled signal $S_1$. In can additionally be desirable to adjust the gain so that other components of the light detection circuit 560 (for example, operational amplifiers) don't saturate or otherwise function improperly or undesirably. The adjustable gain circuit 570 sets the magnitude and polarity of the current signal based on one or more second control signals $Cntrl_2$ (received from, for example, the processing unit 104) and based (directly or indirectly) on the value of the detected signal $I_D$ as described in more detail below.

The light detection circuit 560 also includes an ambient light cancellation circuit 572 configured to provide a countering current signal $I_2$ to at least partially counter an undesired component of the detected signal $I_D$ when the switching circuit 564 may be in the first configuration. The ambient light cancellation circuit 572 sets the magnitude and polarity of the current signal $I_2$ based on one or more third control signals $Cntrl_3$ (received from, for example, the processing unit 104) and based on the value of the signal $S_2$ (for example, a voltage signal) sampled by the second sampling circuit 568, as described in more detail below. For example, as described above, the component of the detected signal $I_D$ to be canceled can be the result of ambient light. That may be, the light detector 562 can receive ambient light in addition to the time-varying scattered light signal $L_S$, and as a result, the detected signal $I_D$ can include an ambient component in additional to the time-varying component resulting from the scattered light signal $L_S$ (It should be noted that, although the ambient light component can vary with time as well, such an ambient light time variance may be of a relatively much lower frequency and effectively "DC" or "static" when compared with the frequency of the time-varying incident light signal $L_E$ and the sampling rate of the first and second sampling circuits 566 and 568, respectively). In some implementations, the light detection circuit 560 also may be configured to adjust a gain of the detected signal $I_D$ to prevent saturation of various electrical components (for example, operational amplifiers) of the light detection circuit 560 or to bring the values of the sampled signal $S_1$ into a range that may be suitable for the ADC 576.

As described above, in some implementations, the light detector 562 may be configured to output the detected signal $I_D$ as a time-varying current signal. In such implementations, the light detection circuit 560 can further include an electrical current-to-voltage converter 574 configured to convert the detected signal $I_D$ to a voltage signal $V_G$. In such implementations, the adjustable gain circuit 570 more specifically sets the current signal $I_1$ to adjust a gain of the voltage signal $V_G$ relative to the first electrical signal $I_D$ when the first switching circuit 564 may be in the first configuration. Additionally, in such implementations, the magnitude and polarity of the current signal $I_1$ are more specifically based on the second control signals $Cntrl_2$ and the voltage signal $V_G$.

In some implementations, the light detection circuit 560 also includes a buffer 578 that buffers the voltage signal $V_G$ and outputs buffer signal $V_S$. The light detection circuit 560 also can include a buffer 580 that buffers the sampled signal $S_1$ prior to input into the ADC 576. The light detection circuit 560 also can include a buffer 582 that buffers the sampled signal $S_2$ prior to input into the ambient light cancellation circuit 572.

In some implementations, the components of the current-to-voltage converter 574 and the adjustable gain circuit 570 form or function as a transimpedance amplifier 584 with variable gain. As described above, such a configuration can avoid or minimize saturation from bright ambient light or bright incident light from the light emitter. For example, as described in more detail below, the gain of the transimpedance amplifier 584 may be automatically increased or decreased with a variable resistors or a multiplexed set or network of resistors in the negative feedback path of the transimpedance amplifier. FIG. 15 shows an example circuit 660 for implementing the light detection circuit 560 of FIG. 14 according to some implementations. For example, the current-to-voltage converter 574 can include a first operational amplifier 674. A first input terminal of the operational amplifier 674 can be electrically coupled with a first terminal of the light detector 652 (for example, a photodiode) and a first terminal $T_1$ of an adjustable impedance stage 670. A second input terminal of the operational amplifier 674 can be electrically coupled with a reference voltage, such as a ground. In the circuit 660, the adjustable gain circuit 570 includes an adjustable impedance stage 670, which may be configured to provide an adjustable impedance. The output terminal of the operational amplifier 674 can be electrically coupled with a second terminal $T_2$ of the adjustable impedance stage 670. The output terminal of the operational amplifier 674 also outputs the voltage signal $V_G$. As described above, the operational amplifier 674 and the adjustable impedance stage 670 form or function as a transimpedance amplifier 684.

In the example implementation, the adjustable impedance stage 670 includes an impedance network having a first impedance path 673a including a resistor having a resistance $R_1$ and a capacitor having a capacitance $C_1$ that provide a first impedance. The impedance network also includes a second impedance path 673b including a resistor having a different resistance $R_2$ and a capacitor having a capacitance $C_2$ that provide a second impedance. The adjustable impedance stage 670 further includes a second switching circuit 671 configured to transition between a first configuration d and a second configuration e to select among the first impedance path 673a and the second impedance path 673b, respectively, based on the one or more second control signals $Cntrl_2$. It should be appreciated that although the circuit 660 includes only two impedance paths, in some other implementations three or more impedance paths can be included and the second switching circuit 671 can select among the three or more impedance paths. Additionally, in some other implementations, rather than having an impedance network having multiple paths of different impedance, the adjustable impedance stage can include a variable impedance, such as an analog component configured to vary an impedance to vary the gain.

In the circuit 660, the ambient light cancellation circuit 572 includes a second adjustable impedance stage 672 between a first terminal $T_3$ of the ambient light cancellation circuit 572 and a second terminal T₄ of the ambient light cancellation circuit 572. The second adjustable impedance stage 672 may be configured to provide an adjustable impedance to adjust the current signal I₂. In the example implementation, the adjustable impedance stage 672 includes an impedance network having a first impedance path 677a including a resistor having a resistance $R_1$. The impedance network also includes a second impedance path 677b including a resistor having a different resistance $R_2$. The adjustable impedance stage 672 further includes a third switching circuit 675 configured to transition between a first configuration d and a second configuration e to select among the first impedance path 677a and the second impedance path 677b based on the one or more third control signals $Cntrl_3$.

Notably, in some implementations, the resistances in the impedance paths 673a and 677a are the same ($R_1$) while the resistances in the impedance paths 673b and 677b are the same ($R_2$). That is, in some implementations, for each impedance path in the adjustable impedance stage 670 of the adjustable gain circuit 570 there may be a corresponding impedance path in the adjustable impedance stage 672 of the ambient light cancellation circuit 572 having the same resistance. Thus, in some implementations, when the second switching circuit 671 may be in configuration d, the third switching circuit 675 also may be in configuration d, and similarly, when the second switching circuit 671 may be in configuration e, the third switching circuit 675 also may be in configuration e. In some implementations, the second switching circuit 671 and the third switching circuit 675 can include the same switching elements or be a part of a single switch (for example, a single analog switch) that controls both the impedance stage 670 and the impedance stage 672. In such implementations, the third control signals $Cntrl_3$ can be the second control signals $Cntrl_2$.

Additionally, as described above with reference to the adjustable impedance stage 670 of the adjustable gain circuit 570, in some other implementations, rather than having an impedance network having multiple paths of different impedance, the adjustable impedance stage 672 of the ambient light cancellation circuit 572 can include a variable impedance, such as an analog component configured to vary an impedance.

In the circuit 660, the buffer 578 includes a second operational amplifier 678. A first input terminal of the second operational amplifier 678 may be electrically coupled with the output terminal of the operational amplifier 674. The output terminal of the second operational amplifier 678 may be electrically coupled with the second input terminal of the second operational amplifier. In some implementations, the circuit further includes an isolation resistor 686, having a resistance $R_{ISO}$, electrically coupled in series between the output terminal of the second operational amplifier 678 and the switching circuit 564. For example, the isolation resistor 686 can serve as a dampening mechanism to minimize ringing.

The first sampling circuit 566 includes a first sample-and-hold (S/H) circuit configured to receive the voltage signal $V_S$, sample a value of the voltage signal $V_S$, and hold (or "maintain," "capture," or "store") the sampled value $S_1$ for a time interval in between consecutive samples. In the circuit 660, the first S/H circuit may be implemented by the switching circuit 564 and a capacitor 666 having a capacitance $C_{S1}$. For example, a first terminal of the capacitor 666 can be electrically coupled to the switching circuit 564 to receive the voltage signal $V_S$ when the switching circuit 564 may be in the first configuration a. The second terminal of the capacitor 666 can be electrically coupled with a reference voltage, such as a ground. When the switching circuit 564 transitions from the first configuration a to, for example, the second configuration b or a third configuration c, the capacitor 666 holds the sampled value $S_1$. In some implementations, it may be desirable to have a large capacitance $C_{S1}$ so that the capacitor 666 may be able to store a lot of charge without leaking appreciably.

In some implementations, because it may be desirable to have a large capacitance $C_{S1}$ (and a large capacitance $C_{S2}$ as described below), it may be desirable to include the first buffer 578, and specifically the operational amplifier 678, to drive the large capacitance of the capacitor 666 (and the capacitor 668 described below). In this way, the first operational amplifier 574 may not have to drive any capacitors and the performance of the operational amplifier 678 may be improved, which could otherwise be destabilized if required to drive a large capacitance.

The ADC 576 may be configured generate and output a digital voltage signal OUT based on the sampled signal $S_1$. As described above, in some implementations, the light detection circuit 560 includes a second buffer 580 for buffering the sampled signal $S_1$. For example, the second buffer 580 can reduce or prevent instability or leakage that may be caused by the ADC 576. In some such implementations, the second buffer 580 includes a third operational amplifier 680. For example, the first input terminal of the third operational amplifier 680 can be electrically coupled to an output of the first sampling circuit 566—the first terminal of the capacitor 666. The output terminal of the third operational amplifier 680 can be electrically coupled with the second input terminal of the third operational amplifier and with the ADC 576.

The second sampling circuit 568 may include a second sample-and-hold (S/H) circuit configured to receive the voltage signal $V_S$, sample a value of the voltage signal VS, and hold the sampled value $S_2$ for a time interval in between consecutive samples. In the circuit 660, the second S/H circuit may be implemented by the switching circuit 564 and a capacitor 668 having a capacitance $C_{S2}$. For example, a first terminal of the capacitor 668 can be electrically coupled to the switching circuit 564 to receive the voltage signal $V_S$ when the switching circuit 564 may be in the second configuration b. The second terminal of the capacitor 668 can be electrically coupled with a reference voltage, such as a ground. When the switching circuit 564 transitions from the second configuration b to, for example, the first configuration a or a third configuration c, the capacitor 668 holds the sampled value $S_2$. Similar to the first sampling circuit 566, in some implementations, it may be desirable to have a large capacitance $C_{S2}$ so that the capacitor 668 may be able to store a lot of charge without leaking appreciably.

As described above, in some implementations, the light detection circuit 560 includes a third buffer 582 for buffering the sampled signal $S_2$ before it may be received by the ambient light cancellation circuit 572, and in the implementation of FIG. 15, by the adjustable impedance stage 672. In some such implementations, the third buffer 582 includes a fourth operational amplifier 682. For example, the first input terminal of the fourth operational amplifier 682 can be electrically coupled to an output of the second sampling circuit 568—the first terminal of the capacitor 668. The output terminal of the fourth operational amplifier 682 can be electrically coupled with the second input terminal of the fourth operational amplifier. The output terminal of the fourth operational amplifier 682 also may be electrically coupled with the ambient light cancellation circuit 572, and more specifically, the adjustable impedance stage 672. In some implementations, the third buffer 582, and more specifically the fourth operational amplifier 682, may be configured to output the sampled signal $S_2$, and more particularly the charge stored on the capacitor 668 associated with the value of the sampled signal $S_2$, to the adjustable impedance stage 672 only when an enable signal EN may be asserted or received. For example, in some implementations, the enable signal EN may be asserted at least during the time interval during which the switching circuit 564 may be in the first configuration a. In this way, while the switching circuit 564 may be in the first configuration a, the charge stored on the capacitor 668 may be transferred in the form of electrical current to the adjustable impedance stage 672 of the ambient light cancellation circuit 572 where it passes through one of the impedance paths 677a or 677b selected by the third switching circuit 675 and results in the current $I_2$ described above.

In some implementations, the circuit 660 further includes a fourth switching circuit 688 coupled with the first terminal of the light detector 562. The fourth switching circuit 688 can be configured to electrically couple the first terminal of the light detector 562 to a voltage reference, such as a ground, based on one or more fourth control signals $Cntrl_4$ (received from, for example, the processing unit 104). In this way, for example, while the light detection circuit 560/660 may be not sampling the detected light signal $I_D$, such as when the switching circuit 564 may be in the second configuration b or the third configuration c, the charge accumulating on the light detector 562 as a result of receiving ambient light can be drained off. In some other implementations, it can be useful for the fourth switching circuit 688 to electrically couple the light detector 562 to a non-ground reference voltage, such as, for example, in implementations in which it may be desirable to reverse bias the light detector 562 (for example, to reverse bias a photodiode).

An example three-stage cycle of operation of the light emission driver circuit 440 and the light detection circuit 560 (and 660) will now be described. It should be appreciated that the stages of the example cycle can encompass intervals of time (as opposed to discreet time points) involving multiple operations or reconfigurations, and can be overlapping with one another in some implementations. In a first stage of operation, the one or more control signals $Cntrl_D$ cause the driver circuit 444 to drive the light emitter 442 to emit the incident light signal $L_E$. Also in the first stage, the one or more first control signals $Cntrl_1$ cause the switching circuit 564 to transition to the first configuration a to enable the first sampling circuit 566 to sample a detected signal $I_D$ (or more specifically a signal derived from the detected signal $I_D$ such as the signal $V_G$ or $V_S$) and subsequently, to enable the ADC 576 to digitize the sampled signal $S_1$ and to output the output signal OUT (including, for example, heart rate data). Also in the first stage, the one or more second control signals $Cntrl_2$ cause the adjustable gain circuit 670 to adjust or select an impedance and to generate the signal $I_1$ to adjust the gain of the voltage signal $V_S$ relative to the detected signal $I_D$. Also at stage 702, the enable signal EN may be asserted causing the charge stored by the second sampling circuit 582 to be transferred via electric current to the ambient light cancellation circuit 572. In response to the one or more third control signals $Cntrl_3$, the ambient light cancellation circuit 572 adjusts or selects an impedance and generates the cancelling signal $I_2$ based on the charge received from the second sampling circuit 582 to cancel (or counter) an ambient component of the detected signal $I_D$. Also in the first stage, the one or more fourth control signals $Cntrl_4$ cause the fourth switching circuit 688 to decouple the light detector 562 from the reference voltage such that the light detector 562 can generate the detected signal $I_D$.

In some implementations, in a second stage of operation, the one or more first control signals $Cntrl_1$ cause the switching circuit 564 to transition to the second configuration b to disable the first sampling circuit 566 and to enable the second sampling circuit 568 to sample the detected signal $I_D$ while the light emitter 442 may be off to, for example, store a charge proportional to an ambient component of the detected signal $I_D$. Also in the second stage, the enable signal EN may be de-asserted to enable the second sampling circuit 582 to store charge (for example, on capacitor 668) associated with the sampled signal $S_2$. As described above, it may be the charge associated with the sampled signal $S_2$ that may be later used to provide the signal $I_D$ to cancel the ambient component of the detected light signal during the first stage of operation.

In some implementations, in a third stage of operation, the one or more fourth control signals $Cntrl_4$ cause the fourth switching circuit 688 to couple the light detector 562 to the reference voltage (for example, a ground) such that the charge that would otherwise accumulate in the light detector 562 due to ambient light can be drained away. In some implementations, the light emission driver circuit 440 and the light detection circuit 560 then repeat the first stage of operation, and so on.

Additional embodiments and details relating to photoplethysmography circuits are disclosed in U.S. patent application Ser. No. 15/223,589, entitled "Circuits and Methods for Photoplethysmographic Sensor," filed on Jul. 29, 2016, the disclosure of which was incorporated by reference in its entirety above.

Display Brightness Level Setting Adjustment

In certain embodiments, the brightness of an electronic display of a biological monitoring device can be adjusted using the ambient light readings from a light detector associated with an optical physiological metric sensor module, such as a phytoplethysmograph (PPG) signal on a wrist worn device. For example, readings from a photodetector that are utilized for PPG generation may be converted to a common reference frame. Such leveraging of existing PPG circuitry and/or components may be more rudimentary than a dedicated front-side ambient light sensor, but may nevertheless provide adequate measurement of lighting conditions. In certain embodiments, ambient data from a PPG sensor may be sufficient for detecting the difference in lighting conditions between indoor and outdoor environments. Therefore, biometric monitoring devices in accordance with the present disclosure can be configured to adjust electronic display brightness settings between at least indoor and outdoor modes, thereby resulting in power savings and extending battery life for the biometric monitoring device.

Generally, electronic displays may be tuned for external visibility in certain devices. For example, the display brightness level may be tuned to have different settings for inside versus outside lighting conditions. In certain embodiments, biometric monitoring devices in accordance with the present disclosure are configured to implement a three-mode brightness level scheme, with low-, intermediate-, and high-light settings. Wherein a PPG sensor is designed to modify detected light signals to account for factors having an effect on PPG calculations/determinations, such modifications may be substantially undone for the purpose of making ambient lighting determinations for display brightness level management. Alternatively, the light detector signal may be obtained by the display brightness level management circuitry before it is processed/modified by the PPG circuitry. In certain embodiments, the display brightness level management circuitry may utilize the modified/processed PPG signals for the purpose of obtaining a more complex solution. In certain embodiments, the display brightness level management and/or PPG circuitry may utilize hysteresis information in processing light detector signals to improve the quality of determinations based thereon.

With further reference back to FIGS. 2 and 3, biometric monitoring devices in accordance with the present disclosure may include an electronic display 230 with a configurable brightness setting. In certain embodiments, the biometric monitoring device 200 is configured to leverage ambient light signals from the optical physiological metric sensor module 243 associated with a backside of the biometric monitoring device 200 to detect indoor/outdoor ambient lighting conditions, thereby allowing for the brightness of the display 230 to be decreased or increased in accordance therewith. In certain embodiments, the display 230 is an organic light-emitting diode (OLED) display. In certain embodiments, display brightness level adjustment based on backside ambient light detection may provide reduced power consumption by up to 50% or more when the display 230 is on and the user is indoors. Such savings may be achieved without the benefit of a front-side dedicated ambient light sensor component, which would generally be associated with increased price, complexity, and battery consumption. Biometric monitoring devices employing display brightness level adjustment in accordance with the present disclosure may further provide an improved user viewing experience compared to displays that always display at a maximum brightness setting, even when used indoors.

The display 230 of FIG. 2 may be representative of an embodiment of the electronic display 130 of FIG. 1, and the biometric monitoring device 200 may be an embodiment of the biometric monitoring device 100. With reference to FIG. 1, the biometric monitoring device 100 includes a brightness level management system 113, which may be configured to adjust a brightness level setting for the electronic display 130. As described above, it may be desirable for the brightness level management module 111 of the control circuitry 110 to adjust the brightness level setting of the electronic display 130 according to an intensity of the environmental ambient light. In certain embodiments, when the ambient light is not greater than a first threshold level, the brightness level management module 111 may maintain the brightness level setting at a low level. In certain embodiments, when the ambient light falls between the first threshold level and a second threshold level, the brightness level setting may be set to an intermediate level. In certain embodiments, when the ambient light is greater than the second threshold, the brightness level setting may be set to a high level. In certain embodiments, only a single ambient light threshold is used, wherein setting the brightness level setting involves setting the brightness level to one of two settings, namely a low mode setting and a high mode setting.

In certain embodiments, the optical physiological metric sensor of the biometric monitoring device runs substantially continuously. In determining the heart rate parameter(s) and/or other physiological metric(s), the optical physiological metric sensor system may make ambient light determinations at any point, or in connection with any process or functionality. For example, in certain embodiments, the optical physiological metric sensor components may be configured to take ambient light readings when the light sources and/or physiological metric (e.g., heart rate) determination circuitry are not active. The use of the physiological metric determination circuitry may be extended to provide ambient light information for display brightness level control purposes. Where the optical physiological metric sensor circuitry is designed to modify the light detector signal(s) to account for skin color or other factors, the display brightness level management circuitry may be configured to reconvert the ambient signal back to the raw ambient signal so as to provide a baseline signal for ambient light determination. For example, PPG circuitry may be designed to apply scaling and/or gain biasing to the light detector signal(s) to account for different lighting conditions, skin tone, or the like; such processing may effectively be reversed to get the raw ambient signal.

In addition to, or as an alternative to, using ambient light information for display brightness level management, certain embodiments disclosed herein provide for the use of such information for determining sun exposure, sleep detection, or the like. In certain embodiments, the PPG circuitry may be configured to store ambient light data values during operation; such values may be used by the display brightness level management subsystem to determine display brightness level settings. In certain embodiments, the PPG sensor runs at a 25 Hz sampling rate. The display brightness level management subsystem may store samples in a circular buffer.

Display Brightness Level Adjustment Processes

Figure 16:
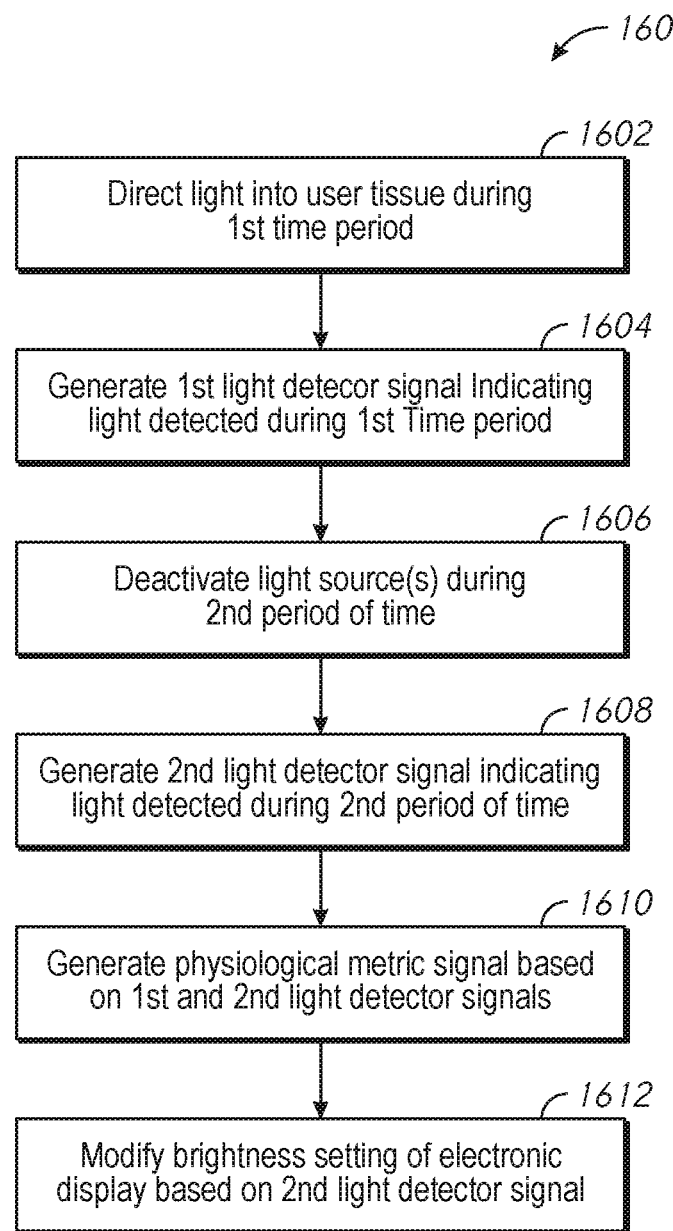
FIG. 16 is a flow diagram illustrating a process for adjusting a backlighting setting of an electronic display according to one or more embodiments.

Certain embodiments disclosed herein provide processes for adjusting a brightness level setting of an electronic display, such as a backlighting setting, for a biometric monitoring device without the use of a dedicated front-side ambient light sensor. Reducing the intensity of display brightness in certain conditions may provide power savings and/or reduce strain on the user's eyes when viewing the display in low-light conditions. FIG. 16 is a flow diagram illustrating a process 1600 for adjusting a brightness level setting of an electronic display according to one or more embodiments. The process 1600 may provide power savings and may be implemented as part of a power management scheme in a biometric monitoring device, such as a wrist-wearable biometric monitoring device.

At block 1602, the process 1600 involves directing light from a light source of a wearable biometric monitoring device into tissue of a user during a first time period. For example, the step of block 1602 may involve activating one or more light sources associated with a backside (i.e., skin-facing when the biometric monitoring device is worn on a user's wrist) of the biometric monitoring device.

At block 1604, the process 1600 involves generating a first light detector signal using a skin-facing light detector, the first light detector signal indicating a first amount of light detected by the light detector during the first period. For example, the first light detector signal may be generated using a photodetector or other light detector, which may be a component of a physiological metric sensor module, such as a module configured to implement optical components for determining heart rate, blood oxygenation, or other physiological metric of the user.

At block 1606, the process 1600 involves deactivating the light source during a second period of time. For example, one or more light sources may be pulsed or otherwise activated and deactivated, wherein the first period of time corresponds with a period during which the light source(s) are active, while the second period of time corresponds to a period during which the light source(s) are deactivated, such that the photodetector(s) do not detect light from the light sources during the second period of time.

At block 1608, the process 1600 involves generating a second light detector signal indicating a second amount of light detected by the light detector during the second period. For example, the second light detector signal may be generated using the light detector utilized in connection with step 1604. Because the light source(s) are not activated during the second period of time, the second light detector signal may provide a reading that indicates ambient light presence, as the light detected during the second period of time is not generally attributable to the light source(s).

At block 1610, the process 1600 involves generating a physiological metric signal based at least in part on the first light detector signal and the second light detector signal. The physiological metric signal may be generated at least in part by generating an ambient light cancellation signal using the second light detector signal, which may be indicative of ambient light because it indicates detected light at a time when the light sources are not activated. The process 1600 may involve cancelling ambient light in the first light detector signal by subtracting out the ambient light indicated by the second light detector signal. Generating the ambient light cancellation signal can involve conditioning the second light detector signal to account for skin tone characteristics of the user, which may be determined in any suitable or desirable way, such as through a calibration process or accessing profile data. In certain embodiments, it may be necessary to at least partially reverse the conditioning of the second light detector signal to produce a raw ambient light signal, which may be used in determining whether or how to modify the display brightness level setting.

At block 1612, the process 1600 involves modifying a brightness setting of an electronic display based at least in part on the second light detector signal. For example, the brightness level may be modified based on the second light detector signal, but not the first light detector signal. Because the second light detector signal may be indicative of ambient light, the utilization of such signal may be used to modify the brightness of the display to account for ambient light conditions. For example, the process 1600 may involve determining whether an amplitude of the raw ambient light signal is greater than a threshold. The ambient light data from the second light detector signal may further be used to determine other metrics, such as sun exposure. Ambient light data determined from the second light detector signal may be stored in a buffer (e.g., circular buffer) or other storage. When the amplitude of the second light detector signal is greater than a threshold, such condition may trigger modifying the brightness of the display to a higher level. In certain embodiments, when the display brightness level management system determines that ambient lighting conditions are high, the high-level brightness level setting may be locked for a period of time, such as until the display and/or biometric monitoring device is powered down or placed in a sleep mode or low-power mode. Locking the brightness level setting may help reduce or prevent unwanted flickering or dimming of the display.

Figure 17:
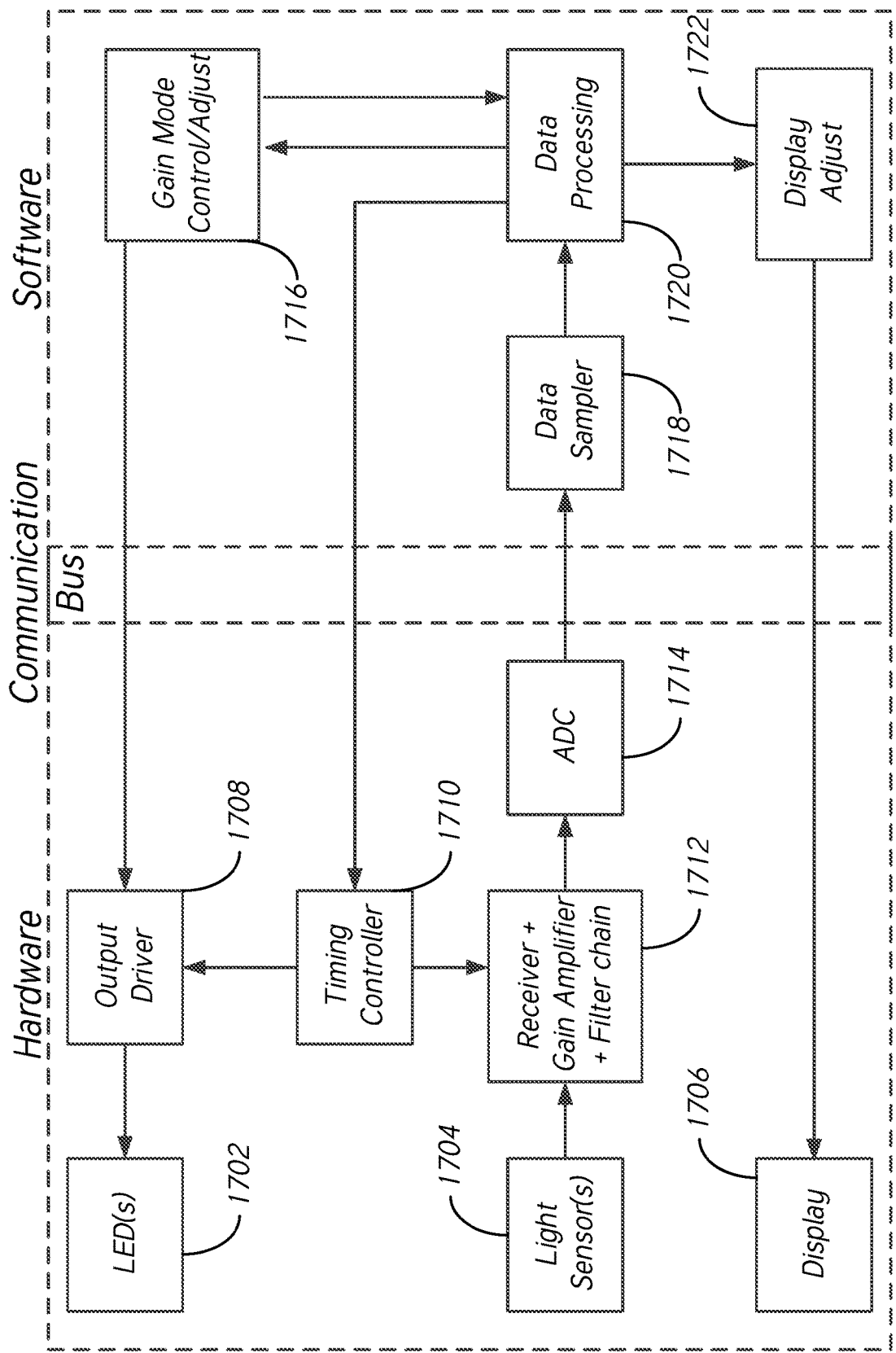
FIG. 17 is a block diagram illustrating an embodiment of a display control feedback system according to one or more embodiments.

FIG. 17 is a block diagram illustrating an embodiment of a display control feedback system according to one or more embodiments. In some embodiments, a display control feedback system includes one or more hardware components, one or more software components and a communication bus to interface between said hardware and software components. In some embodiments, a display control feedback system includes one or more LEDs 1702 or another illumination device or light source. An example display control system may also include an output driver 1708 electrically and/or communicatively coupled to LEDs 1702 and a timing controller 1710. In some embodiments, the display control feedback system includes one or more light sensors 1704 (e.g., light detectors or devices configured to detect light), electrically and/or communicatively coupled to a receiver/gain amplifier/filter chain block 1712. In some embodiments, light sensors 1704 and/or block 1712 include a transducer or another device to convert sensed readings (e.g., illumination) into one or more electrical parameters (e.g., current or voltage). In some embodiments, the circuitry and/or functionality of block 1712 is split across more than one hardware component. For example, block 1712 may represent in FIG. 17 a distinct hardware component for managing reception of detected light/illumination at the one or more light sensors 1704, a distinct hardware component for managing the gain of an amplifier on the receive path of the light control feedback system, and a distinct hardware component for filtering a detected light/illumination value received by the one or more light sensors 1704. The display control feedback system may also include an analog-to-digital converter (ADC) 1714, and a display 1706.

The display 1706, may be electrically and/or communicatively coupled to a display adjust block 1722. A display adjust block 1722 may be electrically and/or communicatively coupled to a data processing block 1720. Data processing block 1720 may be electrically and/or communicatively coupled to several software and/or hardware components, as shown in FIG. 17. For example, data processing block 1720 may be electrically and/or communicatively coupled to gain mode control/adjust block 1716, data sampler block 1718, and timing controller 1710.

In some embodiments, a display control feedback system begins obtaining feedback for a display system by driving one or more LEDs 1702 (e.g., using output driver 1708). As described above, in some embodiments, light from a light source such as LEDs 1702, is transmitted into the skin and/or flesh of a user. In some embodiments, light is received by one or more light sensors 1704. The received light from light sensor(s) 1704 is processed by receiver/gain amplifier/filter chain block 1712. For example, block 1712 may convert a level of determined illumination into an electrical parameter (e.g., voltage and/or current). In some embodiments, block 1712 includes one or more transducer blocks. Processed light/illumination information from the one or more light sensors 1704 may be communicated to ADC 1714, which converts an analog representation of the received light/illumination information into a digital representation passed to data sampler 1718 (e.g., through a communication bus).

In some embodiments, one or more software components operate together to assess received light/illumination information initially received by the one or more light sensors 1704, and correspondingly make adjustments to one or more illumination parameters of LEDs 1702 (or of a light source), and/or adjust one or more reception parameters of the light sensor(s) 1704. The one or more software components may be software modules or blocks residing in a non-transitory computer-readable storage medium, or memory. As an example, the data processing block 1720 may receive sampled illumination information from data sampler 1718 and use the sampled illumination information to determine one or more physiological characteristics of the user. Examples of physiological characteristics that may be determined include, but are not limited to a user's skin tone, level of melatonin in the skin, moisture level of the user's skin and proximity of the skin to the one or more light sensors 1704.

In some embodiments, determining one or more physiological characteristics of a user allows for adjustment of light transmission (e.g., illumination using LEDs 1702) applied to the user's skin and/or flesh, and/or adjustment of light reception (e.g., illumination detection by light sensor(s) 1704).

As shown in FIG. 17, data processing block 1720 may be communicatively coupled to gain mode control/adjust block 1716. Data processing block 1720 may transmit sampled, processed illumination information received from the one or more light sensors 1704 and processed by block 1712 and ADC 1714 and sampled by data sampler 1718, to gain mode control/adjust block 1716. The gain mode control/adjust block 1716 may adjust one or more illumination parameters through an electrical and/or communicative coupling to output driver 1708. For example, gain mode control/adjust block 1716 may instruct output driver 1708 to increase or decrease an applied voltage corresponding to illumination intensity of the one or more LEDs 1702. Additionally, gain mode control/adjust block 1716 may return instructions to data processing block 1720, which may use the instructions to adjust one or more illumination and/or reception parameters, using timing controller 1710. In some embodiments, data processing block 1720 instructs timing controller 1710 to adjust a duration of time for illumination of the one or more LEDs 1702 (e.g., one or more light sources), and/or instructs timing controller 1710 to adjust a duration of time for reception of detected illumination/light at the one or more light sensors 1704 (e.g., one or more light detectors). Although not shown in FIG. 17, in some embodiments, gain mode control/adjust block 1716 is directly coupled electrically and/or communicatively to the receiver/gain amplifier/filter chain block 1712 of the receive path. Whether coupled directly, or indirectly, gain mode control/adjust block 1716 may instruct block 1712 to adjust receiver amplifier gain settings (e.g., by adjusting one or more corresponding register values). Alternatively, or additionally, gain mode control/adjust block 1716 may instruct block 1712 to adjust filtration of the received illumination from light sensor(s) 1704, in the filter chain processing portion of block 1712.

In some embodiments, data processing block 1720 uses the result of a feedback-driven sampled, processed illumination reading to determine one or more operational brightness modes of the display control feedback system. For example, data processing block 1720 may determine that the user is in an environment with an operational brightness mode of 3 out of 6. That is to say, that data processing block 1720 may rank an order of operational brightness modes, based on detected levels of illumination corresponding to each mode. In another example, data processing block 1720 may qualitatively determine that the user is in an indoor lighting setting with dim lights. In some embodiments, the determined operational brightness mode is transmitted by data processing block 1720 to display adjustment block 1722. An operational brightness mode may correspond to a brightness level of display 1706. In some embodiments, display adjust block 1722 uses the operational brightness mode determined by data processing unit 1720 to instruct display 1706 to change a brightness level of display 1706. For example, if the user is in a relatively brightly lit environment, display adjustment block 1722 may instruct display 1706 to increase brightness of display 1706, so that the information on display 1706 is easier to read. In some embodiments, an operational brightness mode corresponds to additional or alternative parameters of display 1706 other than brightness alone, such as but not limited to duration of brightness level and a rate of increase or decrease in illumination.

As described earlier, data processing block 1720 may determine an ambient light level or value. In some embodiments, this determined ambient light level or value corresponds to an operational brightness mode. For example, a measured or determined ambient light level may be compared to one or more threshold values (e.g., level of illumination), to determine a specific operational brightness mode. The determined operational brightness mode may then be used to adjust one or more brightness parameters of display 1706 (e.g., brightness level, rate of illumination). In some embodiments, the determined ambient light level or value is determined with respect to determining or generating a physiological metric (e.g., heart rate) of the user. Data processing block 1720, display adjustment block 1722 and/or an additional processing block (not shown) between blocks 1720 and 1722, may further process an ambient light level or value determined for generating the physiological metric, for purposes of determining display adjustment information. For example, the feedback loop described with respect to FIG. 17 may result in a first value for ambient light level, used by the data processing block 1720 to determine a heart rate for the user. The first ambient light level may further be processed by the data processing block 1720 for purposes of assessing an operational brightness mode, into a second ambient light level (e.g., outdoors and sunny). The additionally processed ambient light level may be a quantitative value (e.g., 3/10) and/or a qualitative value (e.g., dim, indoors).

The one or more LEDs 1702, output driver 1708, timing controller 1710, receiver/gain amplifier/filter chain block 1712, one or more light sensors 1704, display 1706, ADC 1714, gain mode control/adjust block 1716, data processing block 1720, data sampler block 1718 and/or display adjust block 1722 may have one or more characteristics of corresponding modules, blocks, components or units described within this disclosure.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Certain methods and/or processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may be comprised of connected logic units, such as gates and flip-flops, and/or may be comprised of programmable units, such as programmable gate arrays, application specific integrated circuits, and/or processors. The modules described herein are preferably implemented as software modules, but may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

Embodiments of the disclosed systems and methods can be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

Reference throughout this specification to "certain embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics can be combined in any suitable manner, as would be apparent to one of ordinary skill in the art from this disclosure, in one or more embodiments.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A wearable computing device, comprising:
   an electronic display with a configurable brightness level setting;
   a physiological metric sensor system comprising, a light source and a light detector, the light source positioned on a wrist-side of the wearable computing device to direct light into tissue of a user when the user is wearing the wearable computing device on a wrist of the user, the light detector positioned on the wrist-side of the wearable computing device adjacent to the light source to detect light from the light source that reflects back from the user; and
   control circuitry configured to:
      turn the light source on and off;
      collect data via the light detector at least while the light source is off to provide information for evaluation relative to an ambient light level; and
      modify the configurable brightness level setting of the electronic display based at least in part on the ambient light level.

2. The wearable computing device of claim 1, wherein the control circuitry is further configured to:
   determine, one or more physiological characteristics of the user;
   adjust one or more illumination parameters of the light source based on the determined one or more physiological characteristics; and
   adjust one or more reception parameters of the light detector based on the determined one or more physiological characteristics.

3. The wearable computing device of claim 2, wherein the control circuitry is further configured to adjust the one or more reception parameters of the light detector before generating a second light detector signal.

4. The wearable computing device of claim 2, wherein the control circuitry is further configured to adjust the one or more illumination parameters and to adjust the one or more reception parameters before activating the light source during a first period.

5. The wearable computing device of claim 1, wherein the control circuitry is configured to generate light while the light source is turned on using a transimpedance amplifier coupled to sample-and-hold circuitry.

6. The wearable computing device of claim 1, wherein said modifying the configurable brightness level setting comprises changing the configurable brightness level setting associated with a first mode to a second mode.

7. The wearable computing device of claim 6, wherein the first mode corresponds to an outdoor lighting condition and the second mode corresponds to an indoor lighting condition.

8. The wearable computing device of claim 6, wherein the first mode corresponds to an indoor lighting condition and the second mode corresponds to an outdoor lighting condition.

9. The wearable computing device of claim 6, wherein the second mode is associated with a relatively higher brightness level compared to the first mode.

10. The wearable computing device of claim 6, wherein the second mode is associated with a relatively lower brightness level compared to the first mode.

11. The wearable computing device of claim 6, wherein the control circuitry is further configured to lock the configurable brightness level setting of the electronic display in the second mode until the electronic display is powered down.

12. The wearable computing device of claim 6, wherein the first mode and the second mode form a subset of a group of three or more operational brightness modes for the electronic display.

13. The wearable computing device of claim 1, wherein the light source comprises a plurality of LED light sources.

14. A method of managing power in a wearable computing device, the wearable computing device having an electronic display with a configurable brightness level setting, a light source, and a light detector, the light source positioned on a wrist-side of the wearable computing device to direct light into tissue of a user when the user is wearing the wearable computing device on a wrist of the user, the light detector positioned on the wrist-side of the wearable computing device adjacent to the light source to detect light from the light source that reflects back from the user, the method comprising:
  placing the wearable computing device on a wrist of a user;
  turning the light source on and off;
  collecting data via the light detector at least while the light source is off to provide information for evaluation relative to an ambient light level; and
  modifying the configurable brightness level setting of the electronic display based at least in part on the ambient light level.

15. The method of claim 14, further comprising determining an amount of sun exposure of the user based at least in part on the data collected via the light detector at least while the light source is off.

16. The method of claim 14, further comprising storing a value associated with the data collected via the light detector at least while the light source is off in a circular buffer.

17. The method of claim 14, further comprising determining whether an amplitude of a light detector signal representative of the data collected via the light detector at least while the light source is off is greater than a threshold.

18. The method of claim 14, wherein said modifying the configurable brightness level of the electronic display comprises adjusting the configurable brightness level from a first state to a second state.

19. The method of claim 18, wherein the first state corresponds to a low-light mode and the second state corresponds to a high-light mode.

* * * * *